US009802022B2

United States Patent
Smith et al.

(10) Patent No.: US 9,802,022 B2
(45) Date of Patent: Oct. 31, 2017

(54) HUMIDIFICATION OF RESPIRATORY GASES

(75) Inventors: Ian Malcolm Smith, Westleigh (AU); Andrew Roderick Bath, Quakers Hill (AU); Nathan John Row, Coogee (AU); Alexander Virr, Balmain (AU)

(73) Assignee: ResMed Limited, Bella Vista (AU)

( * ) Notice: Subject to any disclaimer, the term of this patent is extended or adjusted under 35 U.S.C. 154(b) by 1851 days.

(21) Appl. No.: 12/397,850

(22) Filed: Mar. 4, 2009

(65) Prior Publication Data

US 2009/0223514 A1 Sep. 10, 2009

Related U.S. Application Data

(60) Provisional application No. 61/034,318, filed on Mar. 6, 2008, provisional application No. 61/042,112, filed
(Continued)

(51) Int. Cl.
*A61M 16/10* (2006.01)
*A61M 16/16* (2006.01)
*A61M 16/00* (2006.01)

(52) U.S. Cl.
CPC ...... *A61M 16/1075* (2013.01); *A61M 16/109* (2014.02); *A61M 16/1095* (2014.02);
(Continued)

(58) Field of Classification Search
CPC .............. A61M 16/10; A61M 16/1075; A61M 16/1085; A61M 16/109; A61M 16/1095;
(Continued)

(56) References Cited

U.S. PATENT DOCUMENTS 1,085,833 A 2/1914 Wilson
2,840,682 A 6/1958 Rubenstein et al.
(Continued)

FOREIGN PATENT DOCUMENTS

AU 14863/95 9/1995
CN 101306218 11/2008
(Continued)

OTHER PUBLICATIONS

Extended European Search Report mailed Jul. 21, 2009 in corresponding European Appln. No. 09003338.2 (9 pages).
(Continued)

*Primary Examiner* — Kathryn E Ditmer
(74) *Attorney, Agent, or Firm* — Nixon & Vanderhye P.C.

(57) ABSTRACT

A humidifier for a respiratory apparatus for delivering a humidified flow of breathable gas to a patient includes a humidifier chamber configured to store a supply of water to humidify the flow of breathable gas, the humidifier chamber comprising a first heating element configured to heat the supply of water; a relative humidity sensor to detect a relative humidity of ambient air and generate signals indicative of the ambient relative humidity; a first temperature sensor to detect a temperature of ambient air and generate signals indicative of the ambient temperature; and a controller configured to determine an absolute humidity of the ambient air from the signals generated by the relative humidity sensor and the first temperature sensor and to control the first heating element to provide a predetermined relative humidity to the flow of breathable gas. A method of humidifying a flow of breathable gas to be provided to a patient includes determining an absolute humidity of ambient air used to form the flow of breathable gas; and controlling a temperature of a supply of water that humidifies the flow of breathable gas to provide a predetermined
(Continued)

absolute humidity corresponding to a predetermined temperature and a predetermined relative humidity of the flow to be delivered to the patient.

65 Claims, 17 Drawing Sheets

Related U.S. Application Data on Apr. 3, 2008, provisional application No. 61/084,366, filed on Jul. 29, 2008.

(52) U.S. Cl.
CPC ........... *A61M 16/16* (2013.01); *A61M 16/161* (2014.02); *A61M 2016/0039* (2013.01); *A61M 2205/3358* (2013.01); *A61M 2205/3365* (2013.01); *A61M 2205/3368* (2013.01); *A61M 2205/3653* (2013.01); *A61M 2205/502* (2013.01)

(58) Field of Classification Search
CPC ......... A61M 16/16; A61M 16/161; F24F 3/14; F24F 6/02; F24F 6/025
USPC ............ 128/203.12, 203.14, 203.16, 203.17, 128/203.26; 123/203.12, 203.14, 203.16, 123/203.17, 203.26
See application file for complete search history.

(56) References Cited

U.S. PATENT DOCUMENTS

| | | |
|---|---|---|
| 2,875,314 A | 2/1959 | Schreyer |
| 3,584,192 A | 6/1971 | Maag |
| 3,659,604 A | 5/1972 | Melville et al. |
| 3,871,373 A | 3/1975 | Jackson |
| 3,982,095 A | 9/1976 | Robinson |
| 3,987,133 A | 10/1976 | Andra |
| 4,014,382 A | 3/1977 | Heath |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,086,305 A | 4/1978 | Dobritz |
| 4,110,419 A | 8/1978 | Miller |
| 4,146,597 A | 3/1979 | Eckstein et al. |
| 4,152,379 A | 5/1979 | Suhr |
| 4,155,961 A | 5/1979 | Benthin |
| 4,201,204 A | 5/1980 | Rinne et al. |
| 4,203,027 A | 5/1980 | O'Hare et al. |
| 4,367,734 A | 1/1983 | Benthin |
| 4,430,994 A | 2/1984 | Clawson et al. |
| 4,532,088 A | 7/1985 | Miller |
| 4,561,287 A | 12/1985 | Rowland |
| 4,621,632 A * | 11/1986 | Bartels .............. A61M 16/1075 128/203.17 |
| 4,657,713 A | 4/1987 | Miller |
| 4,686,354 A | 8/1987 | Makin |
| 4,708,831 A | 11/1987 | Elsworth et al. |
| 4,753,758 A | 6/1988 | Miller |
| 4,829,998 A | 5/1989 | Jackson |
| 4,861,523 A | 8/1989 | Beran |
| 4,865,777 A | 9/1989 | Weiler et al. |
| 4,891,171 A | 1/1990 | Weiler et al. |
| 4,910,384 A | 3/1990 | Silver |
| 4,911,357 A | 3/1990 | Kitamura |
| 4,913,140 A | 4/1990 | Orec et al. |
| 4,921,642 A | 5/1990 | LaTorraca |
| 5,031,612 A | 7/1991 | Clementi |
| 5,062,145 A | 10/1991 | Zwaan et al. |
| 5,092,326 A | 3/1992 | Winn et al. |
| 5,163,423 A * | 11/1992 | Suzuki ..................... 128/203.26 |
| 5,230,331 A | 7/1993 | Rusz et al. |
| 5,231,979 A | 8/1993 | Rose et al. |
| 5,357,948 A | 10/1994 | Eilentropp |
| 5,367,604 A | 11/1994 | Murray |
| 5,368,786 A | 11/1994 | Dinauer et al. |
| 5,392,770 A | 2/1995 | Clawson et al. |
| 5,411,052 A | 5/1995 | Murray |
| 5,429,123 A | 7/1995 | Shaffer et al. |
| 5,445,143 A | 8/1995 | Sims |
| 5,454,061 A | 9/1995 | Carlson |
| 5,468,961 A | 11/1995 | Gradon et al. |
| 5,529,060 A | 6/1996 | Salmon et al. |
| 5,537,996 A | 7/1996 | McPhee |
| 5,537,997 A | 7/1996 | Mechlenburg et al. |
| 5,558,084 A | 9/1996 | Daniell et al. |
| 5,564,415 A | 10/1996 | Dobson et al. |
| 5,588,423 A | 12/1996 | Smith |
| 5,598,837 A | 2/1997 | Sirianne, Jr. et al. |
| 5,640,951 A | 6/1997 | Huddart et al. |
| 5,655,522 A | 8/1997 | Mechlenburg et al. |
| 5,673,687 A | 10/1997 | Dobson et al. |
| 5,694,923 A | 12/1997 | Hete et al. |
| 5,740,795 A | 4/1998 | Brydon |
| 5,769,071 A | 6/1998 | Turnbull |
| 5,800,741 A | 9/1998 | Glenn et al. |
| 5,916,493 A | 6/1999 | Miller |
| 5,937,855 A | 8/1999 | Zdrojkowski et al. |
| 5,947,115 A | 9/1999 | Lordo et al. |
| 5,988,164 A | 11/1999 | Paluch |
| 6,010,118 A | 1/2000 | Milewicz |
| 6,017,315 A | 1/2000 | Starr et al. |
| 6,050,260 A | 4/2000 | Daniell et al. |
| 6,050,552 A | 4/2000 | Loescher et al. |
| 6,078,730 A | 6/2000 | Huddart et al. |
| 6,095,135 A | 8/2000 | Clawson et al. |
| 6,095,505 A | 8/2000 | Miller |
| 6,102,037 A * | 8/2000 | Koch ..................... 128/203.26 |
| 6,116,029 A | 9/2000 | Krawec |
| 6,135,432 A | 10/2000 | Hebblewhite et al. |
| 6,167,883 B1 | 1/2001 | Beran et al. |
| 6,201,223 B1 | 3/2001 | Nitta |
| 6,219,490 B1 | 4/2001 | Gibertoni et al. |
| 6,272,933 B1 | 8/2001 | Gradon et al. |
| 6,335,517 B1 | 1/2002 | Chauviaux et al. |
| 6,338,473 B1 | 1/2002 | Hebblewhite et al. |
| 6,349,722 B1 | 2/2002 | Gradon et al. |
| 6,349,724 B1 | 2/2002 | Burton et al. |
| 6,363,930 B1 | 4/2002 | Clawson et al. |
| 6,367,472 B1 | 4/2002 | Koch |
| 6,394,084 B1 | 5/2002 | Nitta |
| 6,398,197 B1 | 6/2002 | Dickinson et al. |
| 6,435,180 B1 | 8/2002 | Hewson et al. |
| 6,437,316 B1 | 8/2002 | Colman et al. |
| 6,470,885 B1 | 10/2002 | Blue et al. |
| 6,510,848 B1 | 1/2003 | Gibertoni |
| 6,520,021 B1 | 2/2003 | Wixey et al. |
| 6,523,810 B2 | 2/2003 | Offir et al. |
| 6,554,260 B1 | 4/2003 | Lipscombe et al. |
| 6,557,551 B2 | 5/2003 | Nitta |
| 6,584,972 B2 | 7/2003 | McPhee |
| 6,592,107 B1 | 7/2003 | Wong |
| 6,598,604 B1 | 7/2003 | Seakins |
| 6,615,831 B1 | 9/2003 | Tuitt et al. |
| 6,629,934 B2 | 10/2003 | Mault et al. |
| 6,694,974 B1 | 2/2004 | George-Gradon et al. |
| 6,718,973 B2 | 4/2004 | Koch |
| 6,718,974 B1 | 4/2004 | Moberg |
| 6,772,999 B2 | 8/2004 | Lipscombe et al. |
| 6,802,314 B2 | 10/2004 | McPhee |
| 6,827,340 B2 | 12/2004 | Austin et al. |
| 6,877,510 B2 | 4/2005 | Nitta |
| 6,895,803 B2 | 5/2005 | Seakins et al. |
| 6,918,389 B2 | 7/2005 | Seakins et al. |
| 6,935,337 B2 | 8/2005 | Virr et al. |
| 6,953,354 B2 | 10/2005 | Edirisuriya et al. |
| 7,043,979 B2 | 5/2006 | Smith et al. |
| 7,073,500 B2 | 7/2006 | Kates |
| 7,079,758 B2 | 7/2006 | Sunaga et al. |
| 7,086,399 B2 | 8/2006 | Makinson et al. |
| 7,140,367 B2 * | 11/2006 | White et al. ............ 128/204.17 |

(56) References Cited

U.S. PATENT DOCUMENTS

| | | | |
|---|---|---|---|
| 7,146,979 B2* | 12/2006 | Seakins et al. | 128/203.17 |
| 7,291,240 B2 | 11/2007 | Smith et al. | |
| 7,306,205 B2 | 12/2007 | Huddart et al. | |
| 7,413,173 B2 | 8/2008 | DiMatteo et al. | |
| 7,478,635 B2 | 1/2009 | Wixey et al. | |
| 7,677,246 B2 | 3/2010 | Kepler et al. | |
| 8,720,439 B1* | 5/2014 | Kolkowski | A61M 16/16 128/203.12 |
| 2001/0050080 A1 | 12/2001 | Pujol et al. | |
| 2002/0112725 A1* | 8/2002 | Thudor et al. | 128/204.18 |
| 2004/0074493 A1 | 4/2004 | Seakins et al. | |
| 2004/0079370 A1* | 4/2004 | Gradon et al. | 128/203.26 |
| 2004/0102731 A1 | 5/2004 | Blackhurst et al. | |
| 2004/0182386 A1* | 9/2004 | Meier | 128/203.12 |
| 2004/0182392 A1 | 9/2004 | Gerder et al. | |
| 2004/0221844 A1 | 11/2004 | Hunt et al. | |
| 2006/0037613 A1 | 2/2006 | Kwok et al. | |
| 2006/0113690 A1* | 6/2006 | Huddart et al. | 261/129 |
| 2006/0137445 A1 | 6/2006 | Smith et al. | |
| 2006/0191531 A1 | 8/2006 | Mayer et al. | |
| 2006/0213515 A1 | 9/2006 | Bremner et al. | |
| 2006/0269440 A1* | 11/2006 | Lee | F24F 6/02 422/4 |
| 2006/0272639 A1 | 12/2006 | Makinson et al. | |
| 2006/0278221 A1 | 12/2006 | Schermeier et al. | |
| 2007/0051368 A1 | 3/2007 | Seakins et al. | |
| 2007/0079826 A1 | 4/2007 | Kramer et al. | |
| 2007/0125376 A1 | 6/2007 | Reinstadtler | |
| 2007/0169776 A1 | 7/2007 | Kepler et al. | |
| 2007/0230927 A1 | 10/2007 | Kramer | |
| 2007/0283957 A1 | 12/2007 | Schobel (Nee Bauer) et al. | |
| 2007/0284361 A1 | 12/2007 | Nadjafizadeh et al. | |
| 2008/0028850 A1 | 2/2008 | Payton et al. | |
| 2008/0072900 A1 | 3/2008 | Kenyon et al. | |
| 2008/0105257 A1 | 5/2008 | Klasek et al. | |
| 2008/0302361 A1 | 12/2008 | Snow et al. | |
| 2008/0308100 A1* | 12/2008 | Pujol et al. | 128/203.14 |

FOREIGN PATENT DOCUMENTS

| | | |
|---|---|---|
| DE | 33 11 811 A1 | 10/1984 |
| DE | 36 29 353 C1 | 1/1988 |
| DE | 40 34 611 A1 | 5/1992 |
| DE | 94 09 231.1 U1 | 12/1994 |
| DE | 200 18 593 U1 | 2/2001 |
| DE | 10017193 A1 | 11/2001 |
| DE | 202 02 906 U1 | 6/2002 |
| DE | 10 2005 007 773 A1 | 9/2005 |
| EP | 0 097 901 A2 | 1/1984 |
| EP | 0 258 928 A1 | 3/1988 |
| EP | 0 439 950 A1 | 8/1991 |
| EP | 0 885 623 A2 | 12/1998 |
| EP | 1 005 878 A2 | 6/2000 |
| EP | 1 138 341 A2 | 10/2001 |
| EP | 1 479 404 A2 | 11/2004 |
| EP | 1 514 570 A2 | 3/2005 |
| EP | 1 491 226 B1 | 1/2006 |
| EP | 1 197 237 B1 | 1/2007 |
| GB | 2 277 689 A | 11/1994 |
| GB | 2 338 420 A | 12/1999 |
| JP | 57-101952 | 6/1982 |
| JP | 5-71790 A | 3/1993 |
| JP | 5-317428 A | 12/1993 |
| JP | 8-61731 A | 3/1996 |
| JP | 9-234247 A | 9/1997 |
| JP | 10-179746 | 7/1998 |
| JP | 11-57009 A | 3/1999 |
| JP | 2001-314508 A | 11/2001 |
| JP | 2002-95751 A | 4/2002 |
| JP | 2002-286677 A | 10/2002 |
| JP | 2003-245353 | 9/2003 |
| JP | 3673402 B2 | 4/2005 |
| JP | 2005-537083 A | 12/2005 |
| JP | 2007-518451 A | 7/2007 |
| JP | 2008-510510 A | 4/2008 |
| JP | 2008-541830 A | 11/2008 |
| JP | 2009-511218 A | 3/2009 |
| SU | 379270 | 4/1973 |
| WO | 86/02566 | 9/1986 |
| WO | WO 97/47348 | 12/1997 |
| WO | WO 97/47348 A1 | 12/1997 |
| WO | WO 98/04311 A1 | 2/1998 |
| WO | WO 00/21602 A1 | 4/2000 |
| WO | WO 01/13981 A1 | 3/2001 |
| WO | WO 03/055554 A1 | 7/2003 |
| WO | WO 2004/011072 A1 | 2/2004 |
| WO | 2004/020031 A1 | 3/2004 |
| WO | WO 2004/020031 A1 | 3/2004 |
| WO | WO 2004/039444 A1 | 5/2004 |
| WO | WO 2004/105848 A1 | 12/2004 |
| WO | WO 2005/011556 A2 | 2/2005 |
| WO | WO 2005/021076 A2 | 3/2005 |
| WO | WO 2005/079898 A2 | 9/2005 |
| WO | WO 2005/079898 A3 | 9/2005 |
| WO | WO 2006/019323 A1 | 2/2006 |
| WO | WO 2007/045017 A2 | 4/2007 |
| WO | WO 2007/051230 A1 | 5/2007 |
| WO | WO 2007/101298 A1 | 9/2007 |
| WO | WO 2008/148154 A1 | 12/2008 |
| WO | WO 2009/015410 A1 | 2/2009 |

OTHER PUBLICATIONS

Notification of First Office Action mailed Sep. 18, 2012 in Chinese Application No. 200910138707.8, with English Translation (21 pages).

Wiest et al., "In Vivo Efficacy of Two Heated Humidifiers Used During CPAP-Therapy for Obstructive Sleep Apnea Under Various Environmental Conditions," Sleep, vol. 24., No. 4, 2001, Abstract.

Fairchild Semiconductor, "MM74HC74A Dual D-Type Flip-Flop with Preset and Clear," Sep. 1983 (Revised Jan. 2005), pp. 1-8.

TelCom Semiconductor, Inc., "3-Pin µP Reset Monitors," TCM809/810-04, Aug. 29, 1996, pp. 5-15 through 5-18.

Unitrode Products from Texas Instruments, "Current Mode PWM Controller," SLUS224A, Sep. 1994 (Revised Apr. 2002), 11 pages.

National Semiconductor Corporation, "LP339 Ultra-Low Power Quad Comparator," DS005226, Aug. 2000, pp. 1-12.

First Examination Report mailed Dec. 20, 2012 in New Zealand Application No. 604137 (2 pages).

Notice of Reasons for Rejection mailed May 7, 2013 in Japanese Application No. 2009-053840, with English Translation (14 pages).

Patent Examination Report No. 1 issued Mar. 19, 2013 in Australian Application No. 2009200879 (4 pages).

Notification of the Second Office Action mailed Jun. 5, 2013 in Chinese Application No. 200910138707.8, together with English Translation.

Notice of Reasons for Rejection mailed Mar. 11, 2014 in Japanese Application No. 2009-053840, with English Translation (7 pages).

Notification of the Fourth Office Action mailed Jul. 9, 2014 in Chinese Application No. 200910138707.8 with English translation (18 pages).

Decision of Rejection dated Nov. 2, 2014 issued in Chinese Application No. 200910138707.8 with English translation (22 pages).

First Patent Examination Report dated Jun. 26, 2015 issued in Australian Application No. 2014204454 (2 pages).

First Examination Report dated Nov. 18, 2015 issued in New Zealand Application No. 714075 (3 pages).

Notice of Reasons for Rejection dated Feb. 8, 2016 issued in Japanese Application No. 2014-255952 with English translation (6 pages).

Notification of Reexamination dated Mar. 3, 2016 issued in Chinese Application No. 200910138707.8 with English translation (25 pages).

Notification of the First Office Action dated Mar. 14, 2016 issued in Chinese Application No. 201410543100.9 with English translation (21 pages).

Notice of Opposition to Grant of Patent filed Mar. 29, 2016 filed by Fisher & Paykel Healthcare Ltd. (2 pages).

(56) References Cited

OTHER PUBLICATIONS

Statement of Case filed May 25, 2016 filed by Fisher & Paykel Healthcare Ltd. (19 pages).
First Amended Notice of Opposition filed May 25, 2016 filed by Fisher & Paykel Healthcare Ltd. (2 pages).
Evidence of Prior Publication file May 25, 2016 filed by Fisher & Paykel Healthcare Ltd. (3 pages).
Notification of the First Office Action dated Jun. 2, 2016 issued in Chinese Application No. 201510085059X with English translation (8 pages).
Notification of Reexamination dated Aug. 3, 2016 issued in Chinese Application No. 200910138707.8 with English translation (22 pages).
Notice of Allowance dated Aug. 15, 2016 issued in Japanese Application No. 2014-255952 (3 pages).
Second Office Action dated Nov. 30, 2016 issued in Chinese Application No. 2014105343100.9 with English translation (18 pages).
Decision of Reexamination dated Nov. 15, 2016 issued in Chinese Application No. 200910138707.8 with English translation (45 pages).
Deadline for Counterstatement mailed Oct. 31, 2013 in New Zealand Application No. 595304, together with Statement of Case dated Oct. 16, 2013 and Amended Notice of Opposition to Grant of Patent (12 pages).
Notification of the Third Office Action mailed Dec. 23, 2013 in Chinese Application No. 200910138707.8, with English Translation (9 pages).
Office Action dated Mar. 24, 2017 issued in Chinese Application No. 201410543100.9 with English translation (19 pages).
First Examination Report dated May 18, 2017 issued in New Zealand Application No. 731691 (2 pages).
Communication dated May 18, 2017 issued in New Zealand Application No. 625603 (2 pages).
Statutory Declaration of Alex Young in the matter of New Zealand Application No. 625603 in the name of ResMed Limited and in the matter of an Opposition thereto by Fisher & Paykel Healthcare Limited (16 pages).
Translation of DE 100 17 193 A1.
Certificate of Translation of DE 100 17 193 A1.
Office Action dated Jan. 26, 2017 issued in Chinese Application No. 201510085059.X with English translation (16 pages).
Extended Search Report dated Feb. 24, 2017 issued in European Application No. 12162240.1 (12 pages).
Third Office Action dated Jul. 25, 2017 issued in Chinese Application No. 201510085059.X with English translation (9 pages).
Notice of Reasons for Rejection dated Aug. 7, 2017 issued in Japanese Application No. 2016-175411 with English translation (13 pages).

* cited by examiner

HUMIDIFICATION OF RESPIRATORY GASES

CROSS REFERENCE TO RELATED APPLICATIONS

This application claims priority to U.S. Applications 61/034,318, filed Mar. 6, 2008, 61/042,112, filed Apr. 3, 2008, and 61/084,366, filed Jul. 29, 2008, the entire contents of each being incorporated herein by reference.

FIELD OF THE INVENTION

The present invention relates to systems and methods to control the humidity of breathable gases used in all forms of respiratory apparatus ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases.

BACKGROUND OF THE INVENTION

Respiratory apparatuses commonly have the ability to alter the humidity of the breathable gas in order to reduce drying of the patient's airway and consequent patient discomfort and associated complications. The use of a humidifier placed between the flow generator and the patient mask produces humidified gas that minimizes drying of the nasal mucosa and increases patient airway comfort. In addition in cooler climates, warm air applied generally to the face area in and about the mask is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub.

The humidified air may cool on its path along the conduit from the humidifier to the patient, leading to the phenomenon of "rain-out", or condensation, forming on the inside of the conduit. To counter this, it is known to additionally heat the gas being supplied to the patient by means of a heated wire circuit inserted into the patient conduit which supplies the humidified gas from the humidifier to the patient's mask. Such a system is illustrated in Mosby's Respiratory Care Equipment ($7^{th}$ edition) at page 97. Alternatively the heating wire circuit may be located in the wall of the patient conduit. Such a system is described in U.S. Pat. No. 6,918,389.

In a hospital environment, the ambient temperature of the atmosphere within the hospital is controlled by air conditioning to be generally constant at about, for example 23° C. The required temperature for the humidified gases supplied by the respiratory apparatus may thus be controlled within set temperature parameters. The controlled temperature parameters ensure that the humidified gases are held at a temperature above their dew point to prevent condensation within the breathing circuit.

Humidifiers are often used in a home care environment for use such as in the treatment of breathing and sleep apnea disorders. Humidification systems used with CPAP devices for home use have been limited due to pricing constraints, and by the need to maintain the systems small and lightweight, with a comfortable hose and mask, and a low complexity for untrained users. In systems used in clinics or hospitals, such constraints are generally not an issue and temperature and humidity sensors may be located in the airpath and close to the patient's nose to provide direct feedback to control systems, thus ensuring good performance. The cost, size, weight and discomfort of these systems have not been suited to home use. Home users have therefore relied on experience obtained through trial and error to achieve acceptable performance.

In the home care environment, the range of ambient and gas temperatures may well exceed that of the hospital environment. In the home care environment temperatures as low as 10° C. may be present overnight and temperatures over 20° C. may exist during the day. These temperature variations cause the commonly employed control techniques described above to suffer disadvantages. With the types of humidifiers described, condensation (or rain out) in the breathing conduit will exist, at least to some degree. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, create a gurgling sound in the tubing, or may be expelled into the patient. Also, the patient may experience discomfort when breathing gases which are delivered at temperatures widely divergent from that of the ambient temperature. Excessive condensation also results in inefficient usage of the water in the humidifying chamber of the humidifier.

An attempt to solve the problems associated with respiratory systems for home use has involved monitoring ambient temperature and air flow rate as inputs to a control algorithm which predicts corrective heater input to track the user's original setting. This approach, however, still relies on the user to determine an adequate setting for each use condition.

SUMMARY

One aspect is a respiratory apparatus that resolves patient complaints regarding inadequate warmth of the breathable gas delivered to the patient interface, symptoms of nasal dryness, and/or excessive condensation in the air delivery hose.

Another aspect is a respiratory apparatus that permits a patient to select the temperature and/or relative humidity and/or absolute humidity of the breathable gas delivered to the patient interface. In an alternative and/or additional aspect, an absolute humidity at the outlet of a humidifier is controlled to regulate to a predetermined relative humidity delivered to the patient.

A further aspect is a respiratory apparatus that provides a humidified flow to a patient interface at a predetermined temperature and/or humidity while taking into account changing ambient temperature and/or humidity.

A still further aspect is a respiratory apparatus that provides a humidified flow of breathable gas to a patient interface at a predetermined temperature and/or humidity while taking into account changes in the rate of the flow of humidified flow of breathable gas.

Still another aspect relates to a respiratory apparatus comprising a flow generator and a humidifier that are connectable together to permit communication between the flow generator and the humidifier and/or to indicate connection and/or removal.

A further aspect relates to a respiratory apparatus that comprises a humidifier and a heated air delivery tube, hose or conduit. A duty cycle of a heating element of the humidifier and a duty cycle of the heated tube may be controlled so that a combined duty cycle does not exceed 100%, and/or so that the humidifier heating element and the heated tube do not receive power simultaneously. In an alternative and/or additional aspect, the heating element of the humidifier and/or the heated tube regulate a temperature rather than apply a fixed duty ratio. In a further alternative and/or additional aspect, a temperature of the humidified flow of breathable gas in the air delivery tube is measured downstream of the humidifier to regulate to a predetermined relative humidity delivered to the patient.

Another aspect relates to a flow generator that detects the connection of a tube, for example a heated tube, and/or a size of a connected tube, and/or the disconnection of a tube from a humidifier.

Yet another aspect relates to a flow generator that includes constants, such as control parameters, for example stored in a table, that may be trilinearly interpolated to control the humidifier and/or the heated tube.

A further aspect relates to a respiratory apparatus, and a control thereof, including a humidifier and a non-heated tube connectable to the humidifier.

Still another aspect relates to a humidifier control that converts potential measured across, for example, a thermistor, to a temperature.

A further aspect relates to a respiratory apparatus comprising a flow generator and a humidifier that are connectable and may communicate data and/or commands over a serial communications link.

According to a sample embodiment, a humidifier for a respiratory apparatus for delivering a humidified flow of breathable gas to a patient comprises a humidifier chamber configured to store a supply of water to humidify the flow of breathable gas, the humidifier chamber comprising a first heating element configured to heat the supply of water; a relative humidity sensor to detect a relative humidity of ambient air and generate signals indicative of the ambient relative humidity; a first temperature sensor to detect a temperature of ambient air and generate signals indicative of the ambient temperature; and a controller configured to determine an absolute humidity of the ambient air from the signals generated by the relative humidity sensor and the first temperature sensor and to control the first heating element to provide a predetermined absolute humidity to the flow of breathable gas.

According to another sample embodiment, a humidifier for a respiratory apparatus for delivering a humidified flow of breathable gas to a patient comprises a humidifier chamber configured to store a supply of water to humidify the flow of breathable gas, the humidifier chamber comprising a first heating element configured to heat the supply of water; an absolute humidity sensor to detect an absolute humidity of the humidified flow and generate signals indicative of the absolute humidity; and a controller configured to receive the signals from the absolute humidity sensor and control the first heating element to provide a predetermined absolute humidity to the flow of breathable gas.

According to still another sample embodiment, a humidifier for a respiratory apparatus for delivering a humidified flow of breathable gas to a patient comprises a humidifier chamber configured to store a supply of water to humidify the flow of breathable gas, the humidifier chamber comprising a first heating element configured to heat the supply of water; a relative humidity sensor to detect a relative humidity of ambient air and generate signals indicative of the ambient relative humidity; a first temperature sensor to detect a temperature of ambient air and generate signals indicative of the ambient temperature; and a controller configured to determine an absolute humidity of the ambient air from the signals generated by the relative humidity sensor and the first temperature sensor and to control the first heating element to provide a predetermined absolute humidity, a predetermined temperature, and/or a predetermined relative humidity to the flow of breathable gas.

According to yet another sample embodiment, a humidifier for a respiratory apparatus for delivering a humidified flow of breathable gas to a patient comprises a humidifier chamber configured to store a supply of water to humidify the flow of breathable gas, the humidifier chamber comprising a first heating element configured to heat the supply of water; an absolute humidity sensor to detect an absolute humidity of ambient air and generate signals indicative of the ambient absolute humidity; a first temperature sensor to detect a temperature of ambient air and generate signals indicative of the ambient temperature; and a controller configured to control the first heating element to provide a predetermined absolute humidity, a predetermined temperature, and/or a predetermined relative humidity to the flow of breathable gas.

According to a further sample embodiment, a respiratory apparatus for providing a humidified flow of breathable gas to a patient comprises a flow generator to generate a flow of breathable gas and a humidifier as discussed above.

According to a still further sample embodiment, a method of humidifying a flow of breathable gas to be provided to a patient comprises determining an absolute humidity of ambient air used to form the flow of breathable gas; and controlling a temperature of a supply of water that humidifies the flow of breathable gas to provide a predetermined absolute humidity corresponding to a predetermined temperature and a predetermined relative humidity of the flow to be delivered to the patient.

According to another sample embodiment, a humidifier for a respiratory apparatus for delivering a humidified flow of breathable gas to a patient comprises a humidifier chamber configured to store a supply of water to humidify the flow of breathable gas. The humidifier further comprises an inlet configured to receive the flow of breathable gas, a first heating element configured to heat the supply of water, and an outlet configured to deliver the humidified flow of breathable gas to a conduit. A controller is configured to control power supplied to the heating element to provide a predetermined absolute humidity to the humidified flow of breathable gas. The controller continuously adjusts the power supplied to the first heating element in response to changes in ambient conditions and/or the flow of breathable gas to continuously provide the predetermined absolute humidity.

According to still another sample embodiment, a method of humidifying a flow of breathable gas to be provided to a patient comprises determining an absolute humidity of ambient air used to form the flow of breathable gas; and controlling a temperature of a supply of water that humidifies the flow of breathable gas to provide a predetermined absolute humidity to the humidified flow. Controlling the temperature of the supply of water comprises adjusting the temperature of the water supply in response to a change in ambient air temperature, ambient air relative humidity, ambient air absolute humidity, and/or the flow of breathable gas to continuously provide the predetermined absolute humidity.

According to a still further sample embodiment, a method of humidifying a flow of breathable gas to be provided to a patient comprises detecting a temperature of the humidified flow at an end of a delivery hose configured to be connected to a patient interface; generating signals indicative of the temperature of the humidified flow at the end of the delivery hose; and controlling a delivery hose heating element in response to the signals.

According to yet another sample embodiment, a humidifier for a respiratory apparatus for delivering a humidified flow of breathable gas to a patient comprises a humidifier chamber configured to store a supply of water to humidify the flow of breathable gas, the humidifier chamber comprising a first heating element configured to heat the supply of water; an absolute humidity sensor to detect an absolute humidity of ambient air and generate signals indicative of the absolute humidity; and a controller configured to receive the signals from the absolute humidity sensor and control the first heating element to provide a predetermined absolute humidity to the flow of breathable gas. The predetermined absolute humidity corresponds to a predetermined temperature and predetermined relative humidity.

BRIEF DESCRIPTION OF THE DRAWINGS

Sample embodiments will now be described with reference to the accompanying drawings, in which.

DETAILED DESCRIPTION OF ILLUSTRATED EMBODIMENTS

Humidification Theory

Humidity refers to the quantity of water vapor present in air. Humidity is commonly measured in two ways: absolute humidity (AH) and relative humidity (RH). Absolute humidity is the actual content of water recorded in terms of weight per volume. Absolute humidity is usually measured in grams per cubic meter ($g/cm^3$) or milligrams per liter (mg/L).

Relative humidity is the percentage of the actual water vapor content of a gas compared to its capacity to carry water at any given temperature. The capacity of air to hold water vapor increases as the temperature of the air increases. For air with a stable absolute humidity, the relative humidity will decrease as the temperature of the air is increased. Conversely, for air saturated with water (i.e. 100% RH), if the temperature is reduced, excess water will condense out of the air.

Air breathed by humans is heated and humidified by the airways to a temperature of 37° C. and 100% RH. At this temperature, the absolute humidity is about 44 mg/L.

Humidification for CPAP

ISO 8185 requires that a medical humidifier be capable of supplying 10 mg/L AH at a minimum, and 33 mg/L at a minimum if the patient's upper airway is bypassed. These minimum requirements are calculated with the input of dry air. These minimum requirements are also only suitable for short term use. These minimum requirements are often insufficient to minimize symptoms of nasal and upper airways dryness. Under normal operating conditions, the patient or clinician should be able to set the temperature of the air delivered to the patient interface from ambient to about 37° C. If no alarm system or indicator is provided to the respiratory apparatus, in accordance with ISO 8185, sections 51.61-51.8, under normal and single fault conditions, the temperature of the air delivered to the patient interface should not exceed about 41° C.

For CPAP, the upper level of 44 mg/L may not be appropriate because the patient's upper airway is not bypassed. On the other hand, the lower level of 10 mg/L may be too low for CPAP, in particular for patients with mouth leak.

Although no studies have been conducted to determine the minimum level of humidification required for CPAP, Wiest et al. (*Sleep*, Vol. 24, No. 4, pp. 435-440, 2001) found for patients in North America and Europe, the mean absolute humidity of 10 mg/L is too low when CPAP treatment is used without a humidifier system. The study tested two humidifiers which both supplied an absolute humidity of at least 23 mg/L. Wiest et al. concluded that the requirement for CPAP is above the 10 mg/L AH of ISO 8185, but probably below the 23 mg/L AH used in the study. Applicants have determined that an absolute humidity of about 20-30 mg/L provides suitable patient comfort.

Humidifier and Flow Generator

Figure 1:
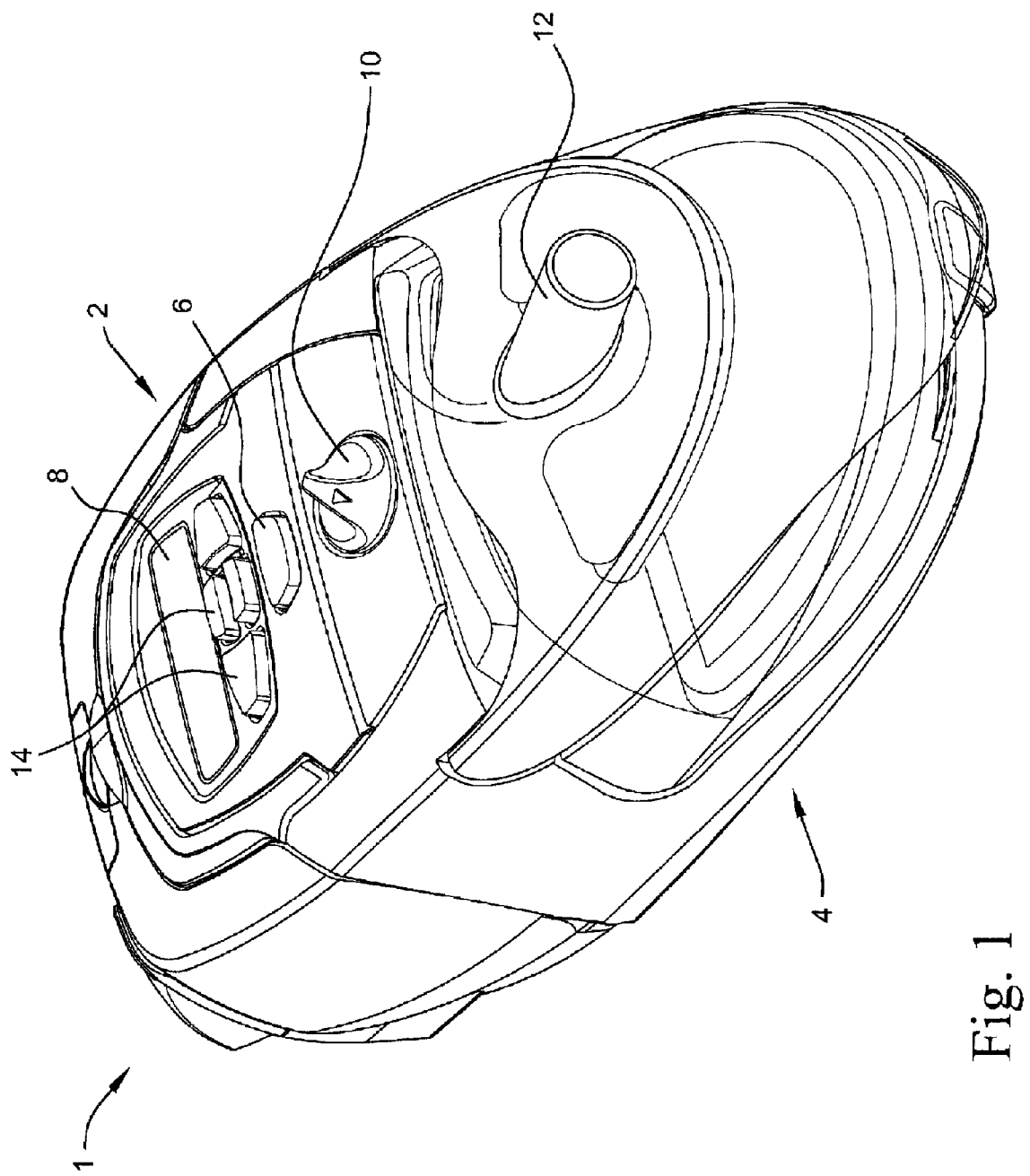
FIG. 1 schematically depicts of a flow generator and humidifier according to a sample embodiment.

Referring to FIG. 1, a respiratory apparatus 1 may comprise a flow generator 2 and a humidifier 4 that are configured to be connectable to each other. Such a flow generator and humidifier combination is disclosed in, for example, WO 2004/112873 A1, the entire contents of which are incorporated herein by reference. The humidifier may also be a humidifier as disclosed, for example, in U.S. Pat. No. 6,935,337, the entire contents of which are incorporated by reference herein.

The flow generator 2 may comprise an ON/OFF switch 6 and a display 8, e.g. an LCD, to display the operational state of the flow generator, and other parameters as described in more detail below. The flow generator 2 may also comprise buttons 14 for controlling the operation of the flow generator 2, for example to select various programs stored in a memory of a controller configured to control operation of the flow generator. The buttons 14 may also be used to set various parameters, e.g., flow rate, of the flow generator 2.

The humidifier 4 may comprise a control knob 10 for controlling power to a heating element (not shown) and setting a temperature at a patient interface as will be discussed in more detail below. Alternatively, the controls for the humidifier 4 may be incorporated within the flow generator 2. The humidifier 4 may also comprise an outlet 12 that is configured for connection to an air delivery hose or conduit for delivering a humidified flow of breathable gas to a patient through a patient interface.

Figure 2:
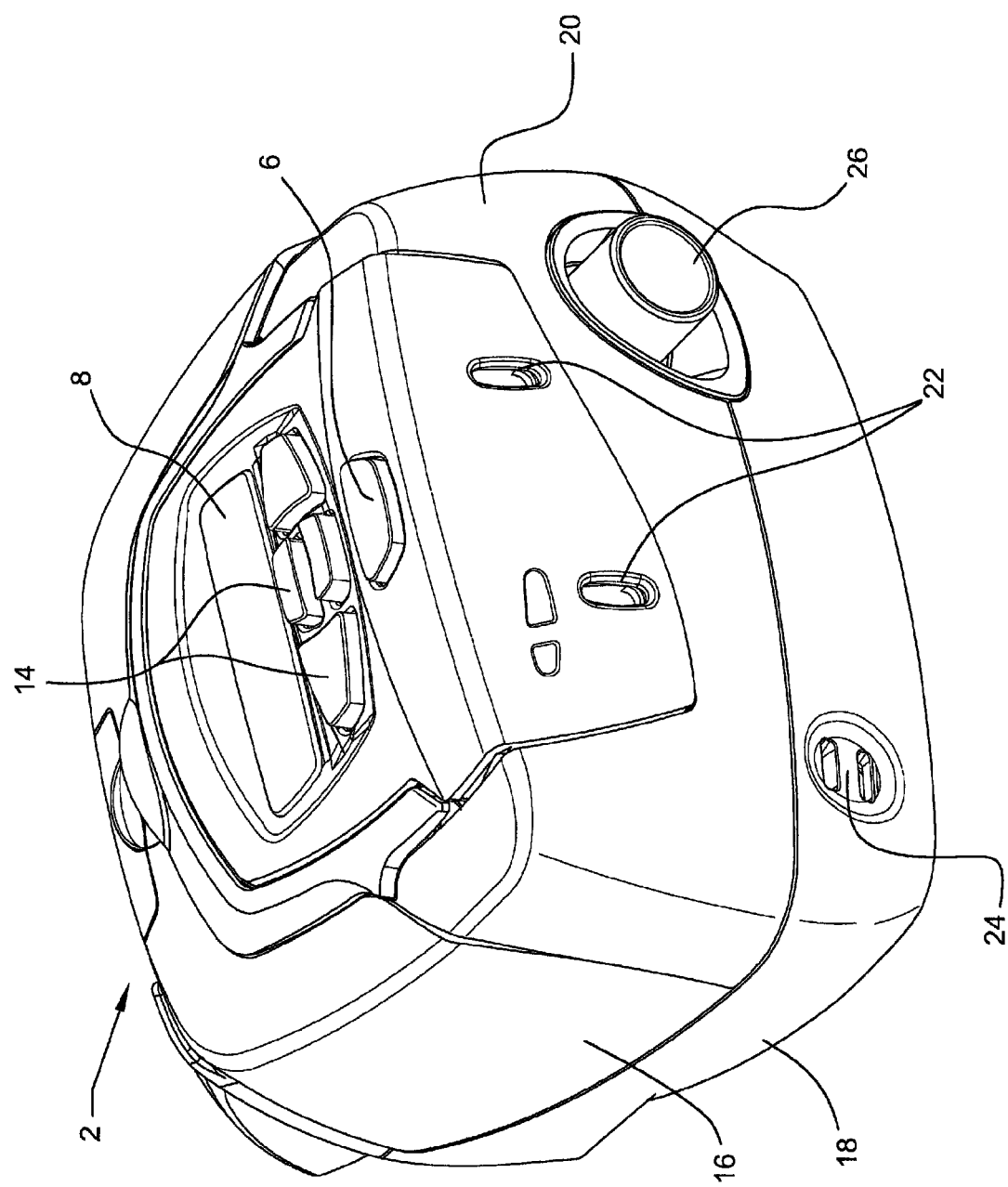
FIG. 2 schematically depicts the flow generator of FIG. 1.

Referring to FIG. 2, the flow generator 2 may be formed of, for example, rigid plastics material molded in two parts, a top case 16 and a bottom case 18. The top case 16 and the bottom case 18 define an engagement face 20 of the flow generator 2 that is configured to engage the humidifier 4 when the humidifier 4 is connected to the flow generator 2. The engagement face 20 includes a pair of slots 22 configured to be engaged by corresponding tongues (not shown) provided on the humidifier 4 by which the flow generator 2 and the humidifier 4 are connected together. An electrical connection 24 may be provided to provide power to the humidifier 4 when the flow generator 2 and the humidifier 4 are connected. The flow generator 2 may further comprise an outlet 26 configured to deliver a flow of breathable gas to the humidifier 4 when the flow generator 2 and humidifier 4 are connected.

Figure 3:
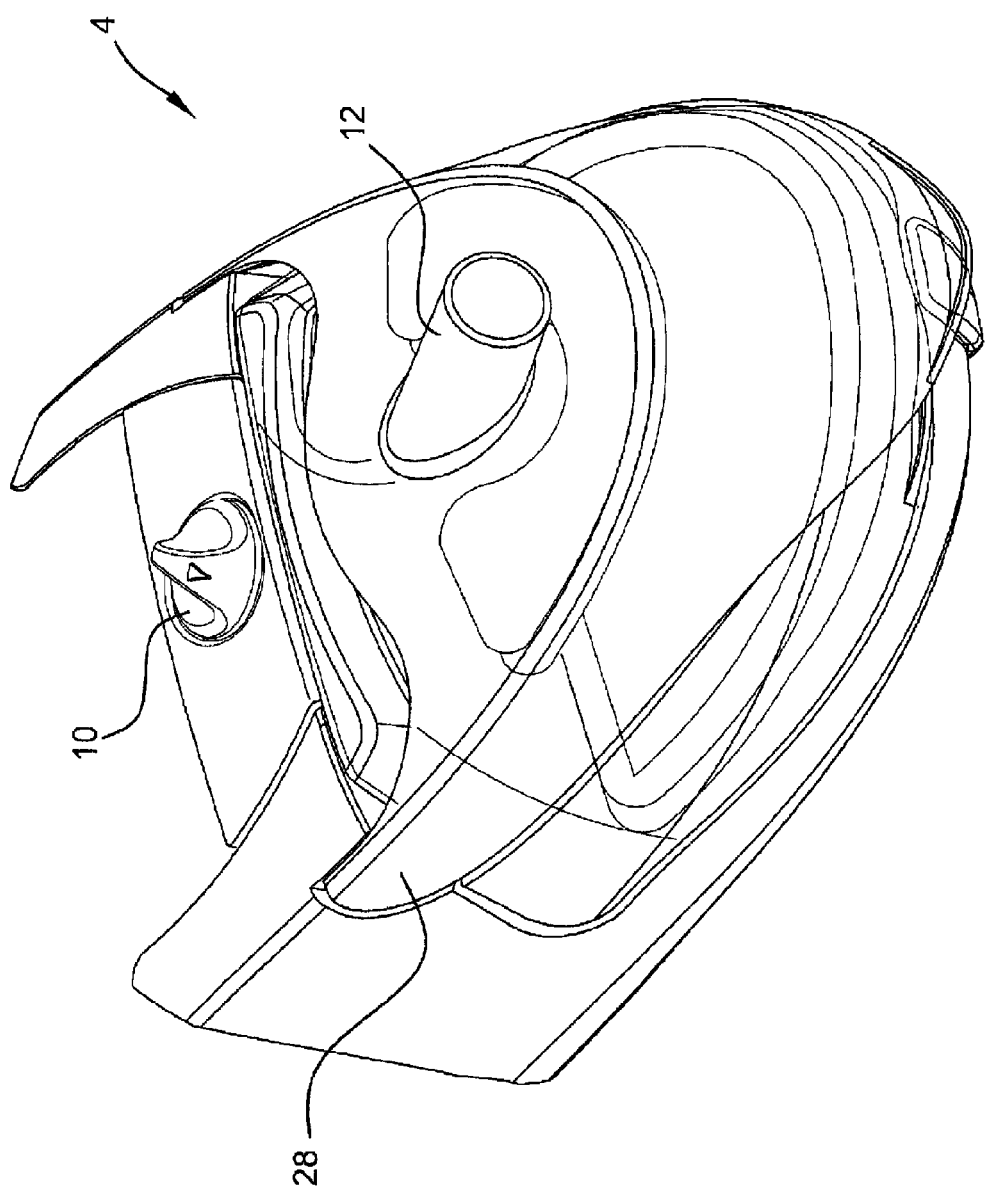
FIG. 3 schematically depicts the humidifier of FIG. 1.

As shown in FIG. 3, the humidifier 4 may comprise a hinged lid 28. The humidifier 4 may also include a tub as disclosed, for example, in U.S. Patent Application Publication 2008/0302361 A1, the entire contents of which are incorporated herein by reference. The humidifier 4 may also include a heating element controllable by the control knob 10. Such a heating element is disclosed, for example, in WO 2008/148154 A1, the entire contents of which are incorporated herein by reference. The humidifier may also be heated, for example, as in WO 2004/112873 A1.

Although the flow generator and humidifier have been disclosed as separate units connectable together to present an integrated unit, it should be appreciated that the flow generator and humidifier may be provided as separate elements that are not connectable together to present an integrated appearance, for example as disclosed in U.S. Pat. No. 6,338,473, the entire contents of which are incorporated herein by reference.

Air Delivery Hose

Figure 4:
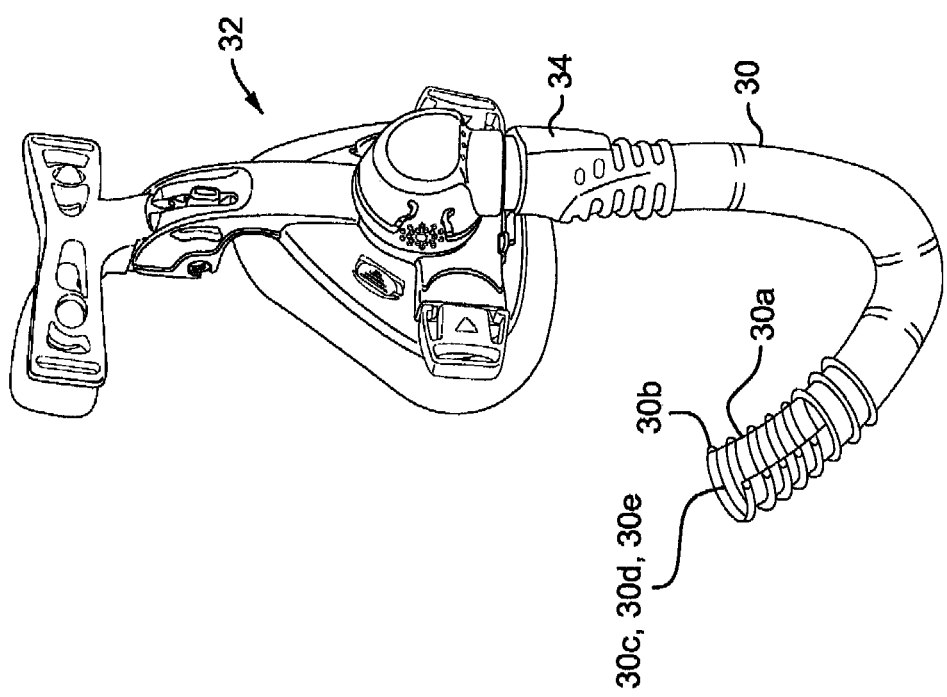
FIG. 4 schematically depicts an air delivery hose and patient interface according to a sample embodiment.

Referring to FIG. 4, an air delivery conduit, or hose, 30 is connected to a patient interface 32, e.g. a mask, to deliver the humidified flow of breathable gas from the humidifier outlet to a patient. It should be appreciated that the patient interface 32 may be a nasal mask, a full face mask, nasal cannulae, pillows or prongs, or a combination of a cushion configured to surround the patient's mouth and nasal prongs or pillows.

The air delivery hose 30 may be a heated tube, for example as disclosed in U.S. Patent Application Publication 2008/0105257 A1, the entire contents of which are incorporated herein by reference. The air delivery hose 30 may be formed by a tube 30*a* formed of, for example, thermoplastic elastomer (TPE), and a helical rib 30*b* formed of, for example, very low density polyethylene. Wires 30*c*, 30*d*, 30*e* are supported by the helical rib 30*b* so as to be in contact with the outer surface of the tube 30*a*. The wires 30*c*, 30*d*, 30*e* may be used to heat the tube 30*a* and to carry signals to and from a controller in flow generator 2 and/or the humidifier 4. It should be appreciated that the air delivery hose 30 may comprise two wires, and the signals may be multiplexed over the two wires. It should also be appreciated that the air delivery hose 30 may include a heating element, for example in the form of a heating strip or wire, as disclosed for example in WO 2009/015410 A1, the entire contents of which are incorporated herein by reference.

The air delivery hose 30 comprises a connector, or cuff 34 that is configured to connect the air delivery hose 30 to the patient interface 32. The patient interface cuff 34 may comprise a temperature sensor, for example a thermistor as disclosed in U.S. Patent Application Publication 2008/0105257 A1, the entire contents being incorporated herein by reference, to sense a temperature of the humidified flow of breathable gas delivered to the patient interface 32.

Figure 5:
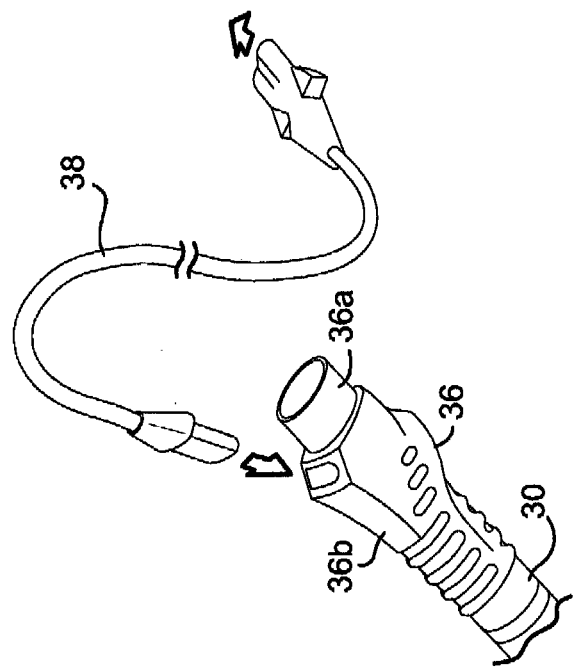
FIG. 5 schematically depicts the air delivery hose of FIG. 4 at an opposite end of the air delivery hose and an electrical connector connectable thereto.

Referring to FIG. 5, the air delivery hose 30 comprises a connector, or cuff 36 that is configured to be connected to the outlet 12 of the humidifier. The humidifier cuff 36 comprises an end 36*a* configured to be connected to the outlet 12 and a grip portion 36*b* to provide a better grip for connecting and disconnecting the air delivery hose 30 to and from the outlet 12.

The humidifier cuff 36 may be connected to a controller of the humidifier 4 by an electrical connector 38. The electrical connector 38 provides power to the wires 30*c*, 30*d*, 30*e* of the air delivery hose 30 to heat the air delivery hose 30 along its length from the humidifier 4 to the patient interface 32.

Respiratory System

Figure 6:
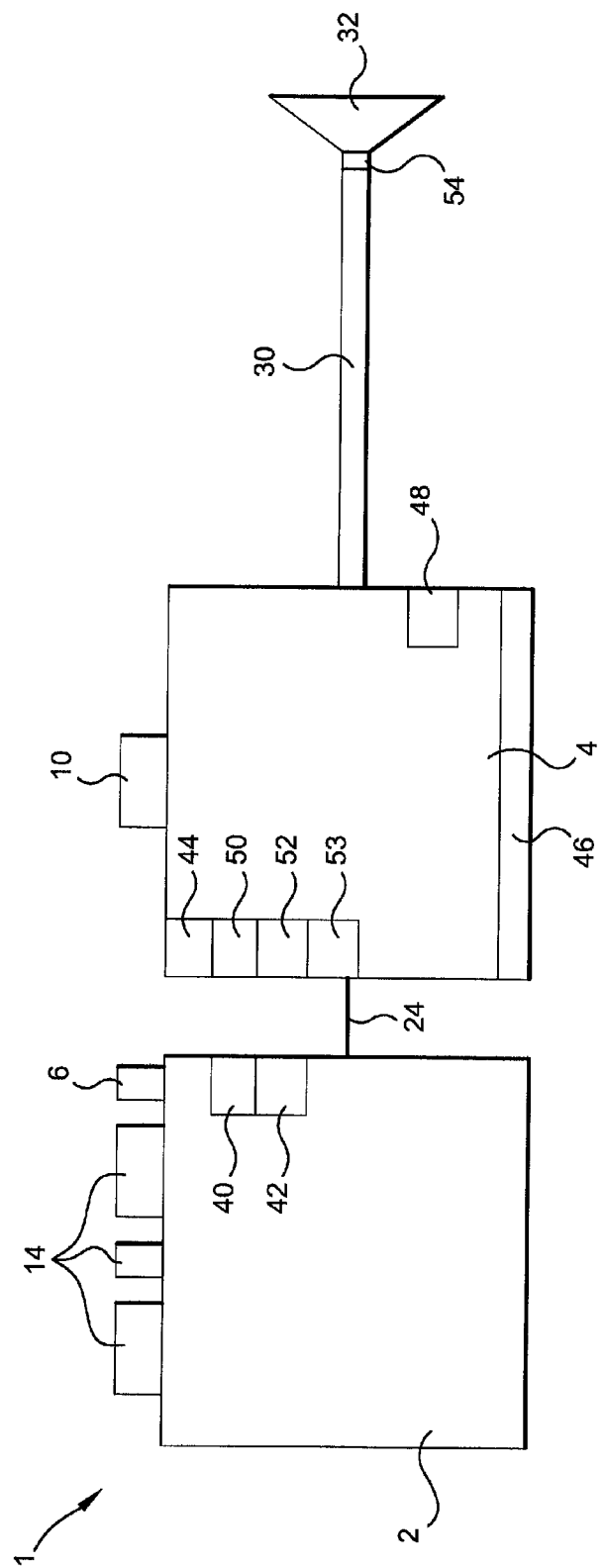
FIG. 6 schematically depicts a respiratory apparatus according to a sample embodiment.

Referring to FIG. 6, a respiratory system according to a sample embodiment of the invention may comprise the flow generator 2, the humidifier 4, and the air delivery hose 30. A patient interface 32 may be connected to the air delivery hose 30.

The flow generator 2 may comprise a controller 40. The flow generator controller 40 may comprise, for example, a programmable logic controller or an application specific integrated circuit (ASIC). The flow generator 2 may further comprise a flow sensor 42 to sense the volume (e.g. L/min.) of the flow of breathable gas generated by the flow generator 2 and delivered to the input of the humidifier 4. It should be appreciated that the flow may be estimated from a speed of a motor of the flow generator rather than provided directly from a flow sensor.

The humidifier 4 may comprise a controller 44. The humidifier controller 44 may be, for example, a programmable logic controller or ASIC. It should be appreciated that, in the case of a flow generator and a humidifier being connectable to form an integrated unit, the flow generator controller and the humidifier controller may be a single controller configured to control both devices. Alternatively, the controller 40 of the flow generator can include all of the functionality of the controller 44 and when the humidifier is attached, the functionality relating to humidification can be accessed from the controller 40.

The humidifier 4 further comprises a heating element 46 configured to heat a supply of water stored in the humidifier 4. The heating element 46 may be, for example, a plate that is provided below a tub of the humidifier. It should also be appreciated that the heating element 46 may comprise a heating element as disclosed, for example, in WO 2009/015410 A1, the entire contents of which are incorporated herein by reference. A temperature sensor 48 may be provided to sense a temperature of the water heated by the heating element 46. It should be appreciated that the temperature of the water may be determined by sensing or measuring the temperature of the heating element 46, for example by using a temperature sensor to directly sense the heating element temperature.

The humidifier 4 may further comprise an ambient temperature sensor 50 to detect the temperature of the ambient air and a relative humidity sensor 52 to detect a relative humidity of the ambient air. The humidifier may also optionally comprise an ambient pressure sensor 53. It should be appreciated that the sensors 50, 52, 53 need not be provided on the humidifier, but may be provided separately, for example from a station that includes the sensors and is connectable to the humidifier 4. It should also be appreciated that the sensors 50, 52, 53 may be provided to the flow generator 2 instead of the humidifier 4, or the ambient temperature, relative humidity, and ambient pressure may be provided from a station to the flow generator 2 instead of the humidifier 4. It should further be appreciated that the flow sensor 42 may be provided to the humidifier 4 instead of, or in addition to, the flow generator 2. It should be even further appreciated that the ambient temperature, relative humidity, and ambient pressure sensors 50, 52, 53 may be replaced by an absolute humidity sensor configured to detect the absolute humidity of the humidified flow, for example at the humidifier outlet, and generate signals indicative of the absolute humidity.

The air delivery hose 30 includes a temperature sensor 54, for example a thermistor, in the patient interface cuff 34. It should be appreciated that the temperature sensor 54 may be provided in the patient interface 32 instead of the cuff 34. The temperature detected by the temperature sensor 54 may be sent as a signal through the air delivery hose 30 to the humidifier controller 44.

The system of FIG. 6 may be configured to allow the patient to select and set a temperature of the humidified flow of breathable gas that is delivered to the patient interface 32. For example, the system may be configured to allow the user to set the temperature of the humidified flow at the patient interface 32 using either the control knob 10 of the humidifier 4 or the control buttons 14 of the flow generator 2. For example, the system may be configured to permit the patient or clinician to select a temperature of the humidified flow at the patient interface of about 10°-37° C., for example about 26° C.-28° C. The system may be configured prevent the patient, or clinician, from selecting and/or setting a temperature that is below ambient temperature. The ambient temperature may be displayed on the display 8 of the flow generator, or a message may be displayed that indicates to the patient or clinician that the selected temperature is invalid as it is below the ambient temperature. Alternatively, the system may allow selection of an automatic, or default, temperature setting of, for example, 27° C.

The system of FIG. 6 may also be configured to provide an absolute humidity to the patient interface 32 that is between, for example, about 10-44 mg/L. The relative humidity of the flow at the patient interface may be controlled to have less than 100% RH, for example about 70-90% RH, for example about 80% as a default setting. Keeping the relative humidity of the flow in the air delivery hose 30 below 100% RH helps to prevent rain out in the air delivery hose between the humidifier 4 and the patient interface 32. The system may also be configured to provide an automatic, or default, relative humidity at the patient interface 32, for example 80%. The system may also be configured to allow the patient or clinician to set the relative humidity of the flow at the patient interface 32. Although the relative humidity of the flow at the patient interface 32 may be detected directly by a humidity sensor placed in the patient interface, as humidity sensors are prone to misread or malfunction in the presence of condensation, a more reliable approach may be to detect the relative humidity and the temperature of the ambient air, or the incoming gas flow, and calculate the absolute humidity.

The system of FIG. 6 may compensate for a wide variation of ambient temperature and humidity. The temperature of the flow at the patient interface 32 may be detected directly, for example by the temperature sensor 54. The relative humidity of the flow at the patient interface may be calculated from: 1) the water content of ambient air (from its ambient temperature and relative humidity); 2) the temperature of the water in the humidifier tub (e.g. as detected by the temperature sensor 48); and/or 3) the flow rate through the humidifier tub (e.g. as detected by the flow sensor 42 of the flow generator). It should be appreciated that the relative humidity may also be detected directly, for example by a relative humidity sensor at the end of the tube 30, or in the patient interface 32.

The temperature of the flow at the patient interface 32 may be controlled by controlling the power supplied to the air delivery hose 30, e.g., by controlling the current to the wires of the hose 30. The relative humidity of the flow at the patient interface 32 may be controlled by the temperature of the water in the humidifier tub, taking the ambient temperature, the ambient relative humidity, and flow rate as input parameters.

Humidity Control

Figure 7:
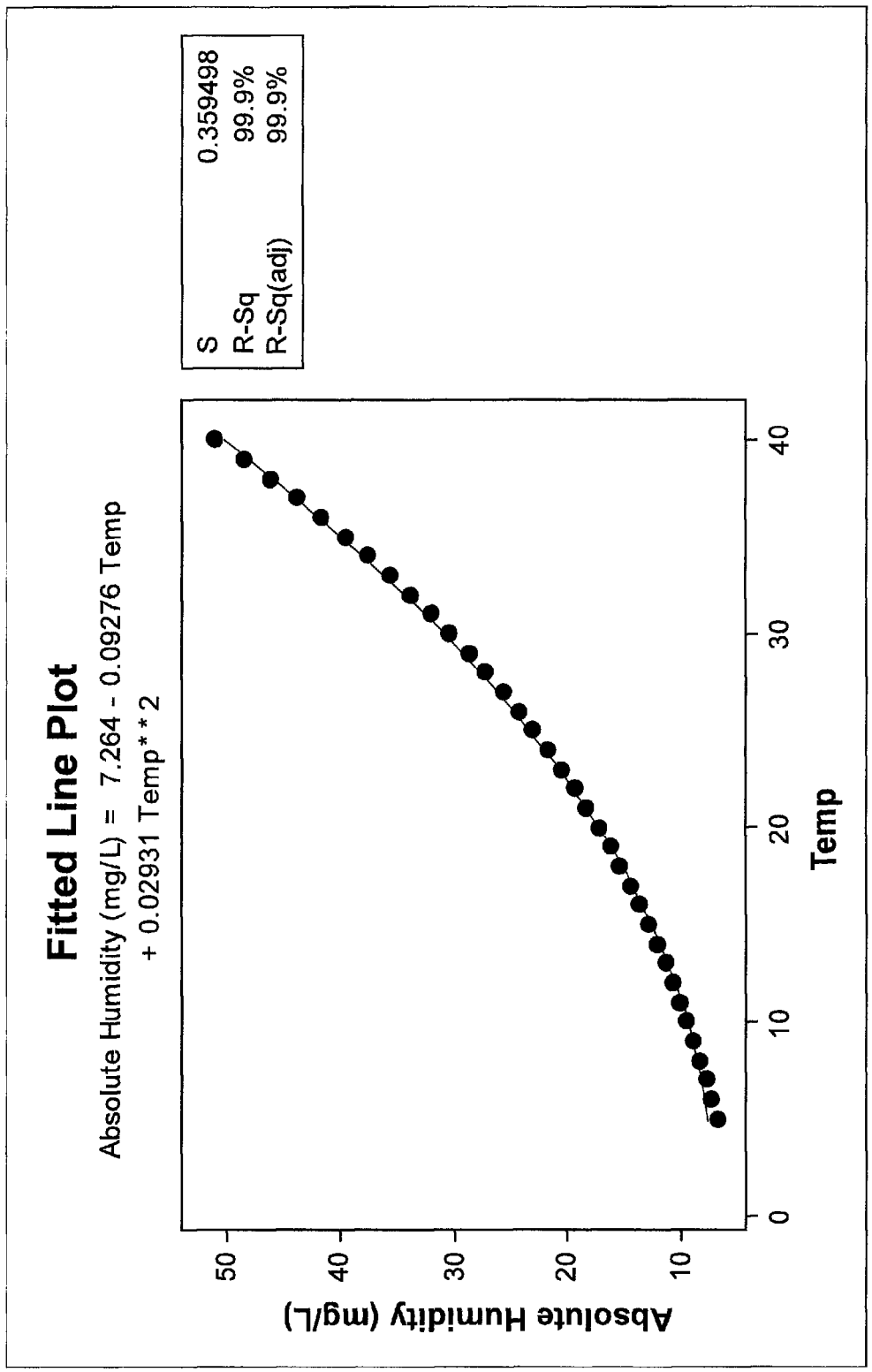
FIG. 7 schematically depicts a relationship between absolute humidity of ambient air and temperature of ambient air at saturation with water vapor.

Referring to FIG. 7, the absolute humidity of saturation of ambient air can be calculated from the psychrometric properties of water vapor. See, for example, *Heat Transfer*, Y. Cengel, McGraw-Hill, 1998 (pp. 958-59, table A9). See also, for example, *Release on the IAPWS Industrial Formulation 1997 for the Thermodynamic Properties of Water and Steam*, The International Association for the Properties of Water and Steam, September, 1997, Erlangen, Germany. As shown in FIG. 7, the absolute humidity is expressed in mg/L, i.e., mass of water vapor per volume of air, where the conditions are ambient temperature and standard (sea level) pressure, or ATPS. The absolute humidity AHa of the ambient air may be defined by any equation or look-up table that corresponds to the psychrometric properties of water vapor. For example, the following quadratic equation:

$$AHa = RHa \cdot (K_1 - K_2 \cdot Ta + K_3 \cdot Ta^2) \qquad (1),$$

where RHa is the relative humidity of the ambient air, Ta is the temperature of the ambient air, and $K_1$, $K_2$, and $K_3$ are coefficients. For example, coefficients K1, K2, K3 may be empirically determined, such as by curve fitting to available data. $K_1$ may be equal to 7.264, $K_2$ may be equal to 0.09276, and $K_3$ may be equal to 0.02931, for example.

The target temperature Tm of the flow at the mask and the target relative humidity RHm at the mask similarly determine the absolute humidity AHm at the mask, as defined by the following equation:

$$AHm = RHm \cdot (K_1 - K_2 \cdot Tm + K_3 \cdot Tm^2) \qquad (2),$$

wherein $K_1 = 7.264$, $K_2 = 0.09276$, and $K_3 = 0.02931$, for example.

The difference ΔAH between the ambient absolute humidity AHa, as determined by equation (1), and the mask absolute humidity AHm, as determined by equation (2), is equal to the absolute humidity to be added to the flow by the humidifier 4. Of course, if AHm<AHa, no humidification is required. Given the flow rate F (L/min) through the humidifier tub, the evaporation rate E of water may be determined using an equation derived by characterizing the response of the humidifier. For example, in one embodiment the evaporation rate may be determined from the flow rate and change in absolute humidity by the following equation:

$$E(g/hr) = \Delta AH(mg/L) \cdot F(L/min) \cdot (60 \text{ min/hr}) \cdot 0.001 \text{ g/mg} \qquad (3).$$

As an example, for a CPAP treatment using the system of FIG. 6, a pressure of 10 cm $H_2O$ is to be supplied to treat a patient with OSA. At 10 cm $H_2O$, the flow rate F is about 35 L/min, which is equivalent to the mask vent flow at the prescribed pressure. At an ambient temperature Ta of 20° C. and an ambient relative humidity RHa of 50%, the absolute humidity AHa of the air entering the humidifier, from equation (1), is equal to 0.5·17.3=10.4 mg/L. Assuming the patient selects a mask temperature Tm of 25° C. and a relative humidity of 90% is selected, or automatically set, the absolute humidity AHm at the mask, from equation (2) is equal to 0.9·23.3=20.9 mg/L. The absolute humidity ΔAH to be added by the humidifier is equal to 20.9−10.4=10.5 mg/L. The evaporation rate E from the humidifier, from equation (3) is thus determined as E=(10.5 mg/L)·(35 L/min)·(60 min/hr)·(0.001 g/mg)=22 g/hr.

The evaporation rate of water is related to its vapor pressure, driven by the temperature of the liquid water. Generally speaking, each 10° C. rise in water temperature almost doubles the saturation vapor pressure. See, for example, *Heat Transfer*, Y. Cengel, McGraw-Hill, 1998 (pp. 958-59, table A9). See also, for example, *Release on the IAPWS Industrial Formulation 1997 for the Thermodynamic Properties of Water and Steam*, The International Association for the Properties of Water and Steam, September, 1997, Erlangen, Germany. In addition, the ambient air water content, i.e. the vapor pressure of water already in the ambient air, as determined from the ambient air temperature and ambient air relative humidity, reduces the evaporation rate. The atmospheric pressure of the ambient air also effects the evaporation rate, but less so than the rise in water temperature and the ambient air water content. Water vapor evaporates more rapidly at lower atmospheric pressure, e.g. at higher altitudes.

The temperature of the water in the humidifier tub may be subjected to closed-loop control. Alternatively, the temperature of the heating element under the water maybe subjected to closed-loop control. Other parameters may contribute to the setpoint for the closed-loop control. For example, the evaporation rate E is limited by saturation of water vapor in the humidifier tub. The saturation of water vapor in the tub depends on the temperature of the air flowing into the humidifier from the flow generator. The flow generator may increase the temperature of the air flowing into the humidifier, e.g. from heat generated by the flow generator motor.

The theoretical relationship between the evaporation rate and the temperature of the water also assumes that the water vapor in the humidifier tub is efficiently removed from the tub. However, the pattern of airflow through the tub may bypass some pockets where water vapor is generated. In addition, a stirring action from the airflow may distribute heat evenly through the water in the tub.

The theoretical relationship also assumes that the evaporation rate is largely unaffected by the temperature of the air in the tub until saturation is reached. In practice, chilling the surface of the water, for example by a decrease in the ambient air temperature, may reduce the evaporation rate. Temperature gradients exist from heating the tub through the water and walls of the tub to the outside of the humidifier. These temperature gradients may contribute inconsistencies between the sensed temperature and the actual temperature at the surface of the water. Even if a temperature sensor is not used, the temperature gradients may contribute to inconsistencies between the temperature of the body of water and the temperature of the surface of the water. The evaporation rate is related to the temperature at the water surface.

EXAMPLE 1

Adjustment to Change in Ambient Temperature with Mask Temperature Controlled

In this example, the system of FIG. 6 is set to deliver saturated air to the mask at 30° C. The temperature may be set by the patient, or clinician, by use of the control buttons 14 of the flow generator 2 and/or the control knob 10 of the humidifier 4. The absolute humidity of the ambient air is 10 mg/L, which does not change as the temperature of the ambient air changes, for example in the patient's bedroom, during the patient's sleep. As shown in Table 1, the temperature of the water in the humidifier tub is adjusted to achieve 100% RH air at the patient interface.

In this comparative example, although the relative humidity of the air delivered to the patient interface is 100% RH for all temperatures, the absolute humidity of the air delivered to the patient interface varies widely, for example from 12.5 mg/L-30.7 mg/L. The temperature of the air flow delivered to the patient interface also varies according to the

TABLE 1

| Water temperature deg C. | Air temperature deg C. | Air absolute humidity (mg/L) | Air relative humidity | Humidification output mg/L | Temperature of air delivered | Humidity of air delivered (mg/L) | Humidity of air delivered % RH |
|---|---|---|---|---|---|---|---|
| 64.9 | 15 | 10 | 80% | 20.7 | 30 | 30.7 | 100% |
| 64.9 | 16 | 10 | 75% | 21.0 | 30 | 31.0 | 100% |
| 64.7 | 17 | 10 | 71% | 20.9 | 30 | 30.9 | 100% |
| 64.5 | 18 | 10 | 66% | 20.9 | 30 | 30.9 | 100% |
| 64.3 | 19 | 10 | 62% | 20.7 | 30 | 30.7 | 100% |
| 64.3 | 20 | 10 | 58% | 20.8 | 30 | 30.8 | 100% |
| 64.2 | 21 | 10 | 55% | 20.7 | 30 | 30.7 | 100% |
| 64.3 | 22 | 10 | 52% | 20.9 | 30 | 30.9 | 100% |
| 64.3 | 23 | 10 | 48% | 20.9 | 30 | 30.9 | 100% |
| 64.3 | 24 | 10 | 46% | 20.9 | 30 | 30.9 | 100% |
| 64.3 | 25 | 10 | 43% | 20.8 | 30 | 30.8 | 100% |
| 64.3 | 26 | 10 | 41% | 20.8 | 30 | 30.8 | 100% |
| 64.3 | 27 | 10 | 38% | 20.7 | 30 | 30.7 | 100% |
| 64.4 | 28 | 10 | 36% | 20.8 | 30 | 30.8 | 100% |
| 64.5 | 29 | 10 | 34% | 20.8 | 30 | 30.8 | 100% |
| 64.5 | 30 | 10 | 32% | 20.7 | 30 | 30.7 | 100% |

Figure 8:
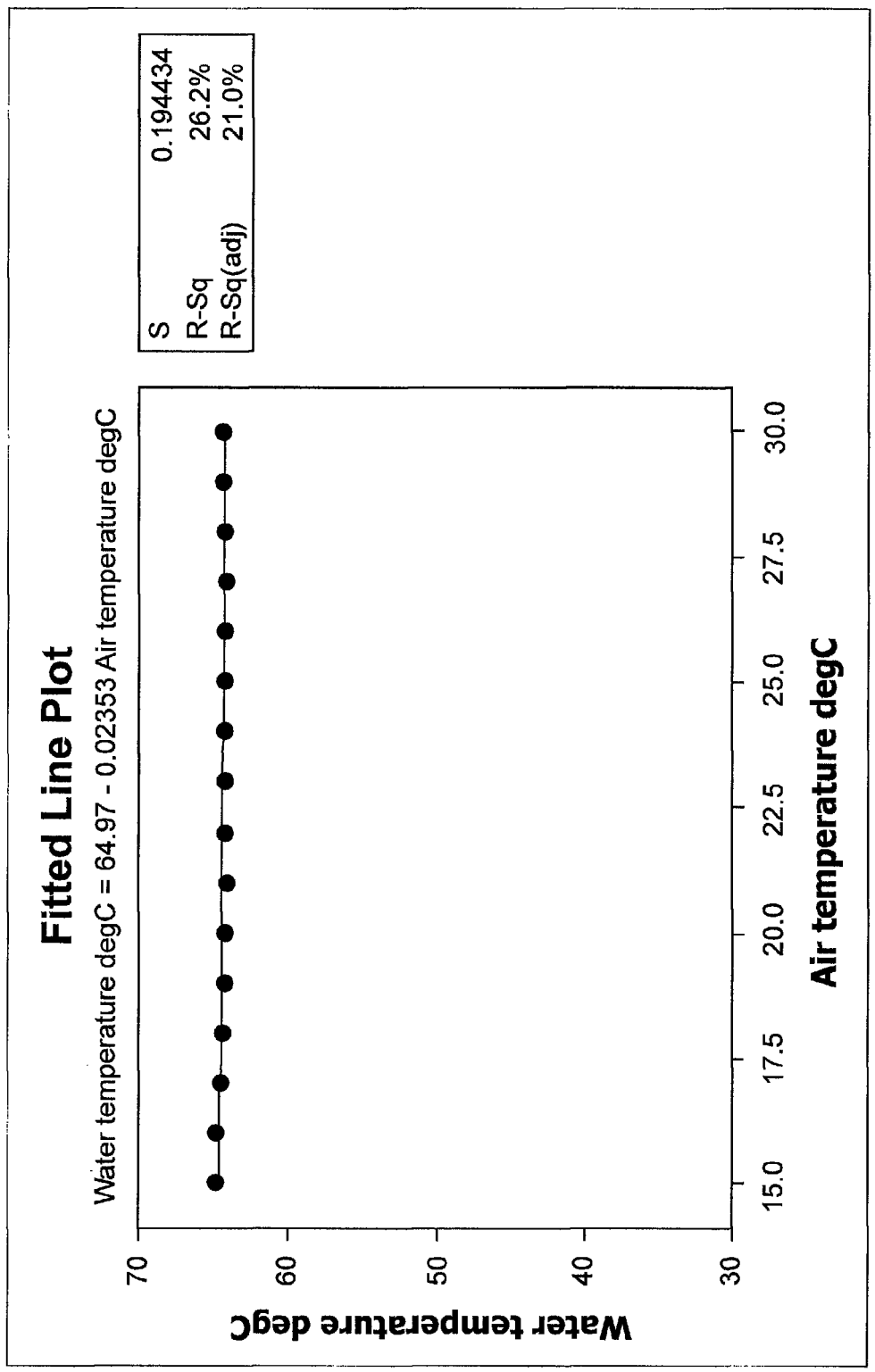
FIG. 8 schematically depicts a relationship between the temperature of water in a humidifier tub and ambient air temperature where there is no change in ambient absolute humidity according to one example.

As shown in FIG. 8, the result of the closed-loop control is that the temperature of the water in the tub must be held to about the same setpoint, regardless of the ambient temperature of the air in the room. Thus, there is no need for the system to respond to changes in the ambient air temperature if the temperature at the mask is regulated.

ambient air temperature. The patient thus is unable to increase the temperature of the air flow delivered to the patient interface.

COMPARATIVE EXAMPLE 1

Adjustment to Change in Ambient Temperature with Mask Temperature Uncontrolled

Figure 9:
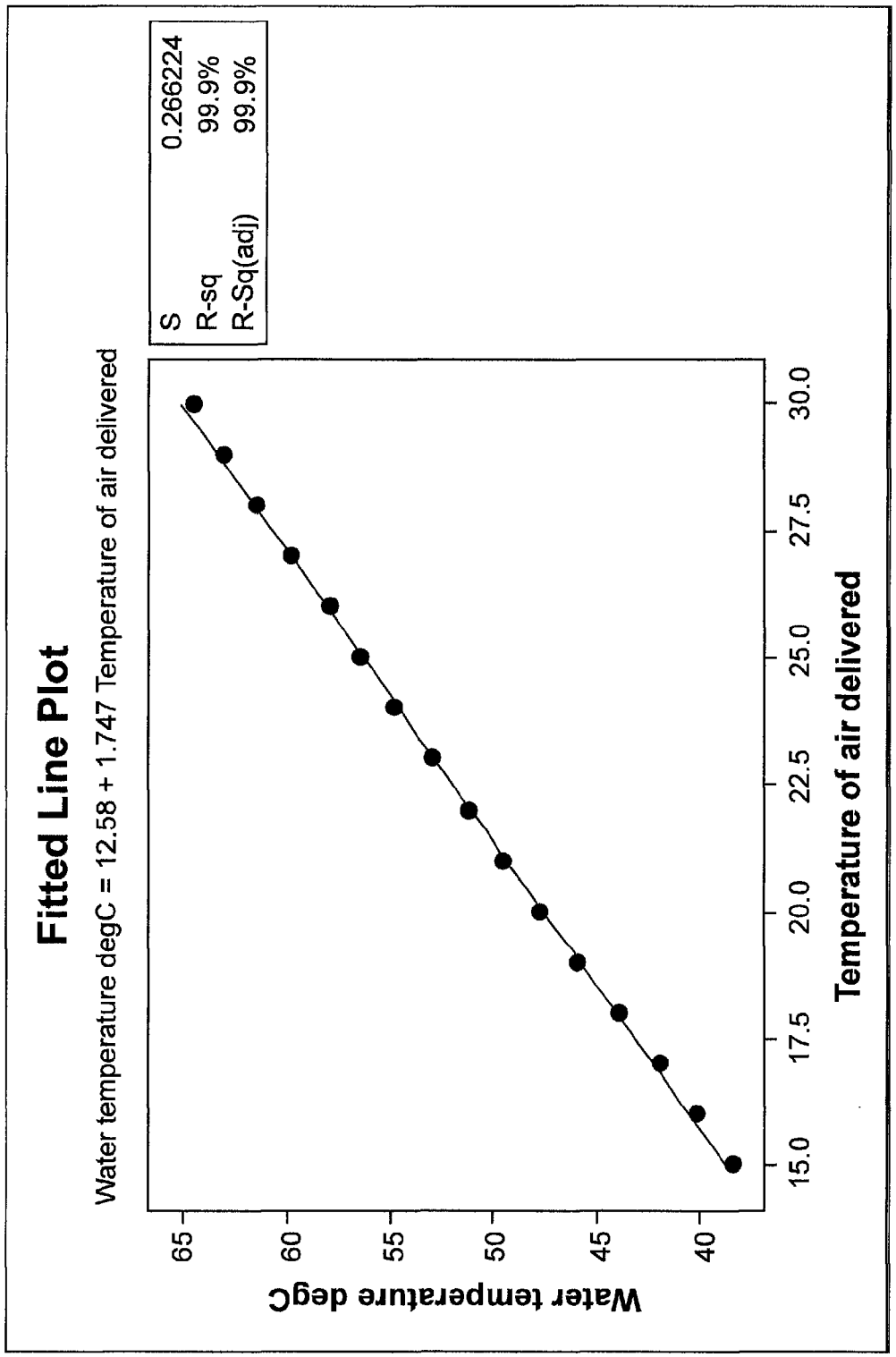
FIG. 9 schematically depicts a relationship between the temperature of water in a humidifier tub and the temperature of an air flow delivered to a patient interface and ambient temperature where there is no change in ambient absolute humidity according to a comparative example.

In this comparative example, the temperature of the air delivered to the patient interface is not under a feedback control loop. Instead, the system is controlled so that the temperature of the water in the humidifier tub was controlled to track the ambient air temperature, as shown in Table 2 and FIG. 9.

EXAMPLE 2

Adjustment to Change in Set Temperature at Patient Interface

Figure 10:
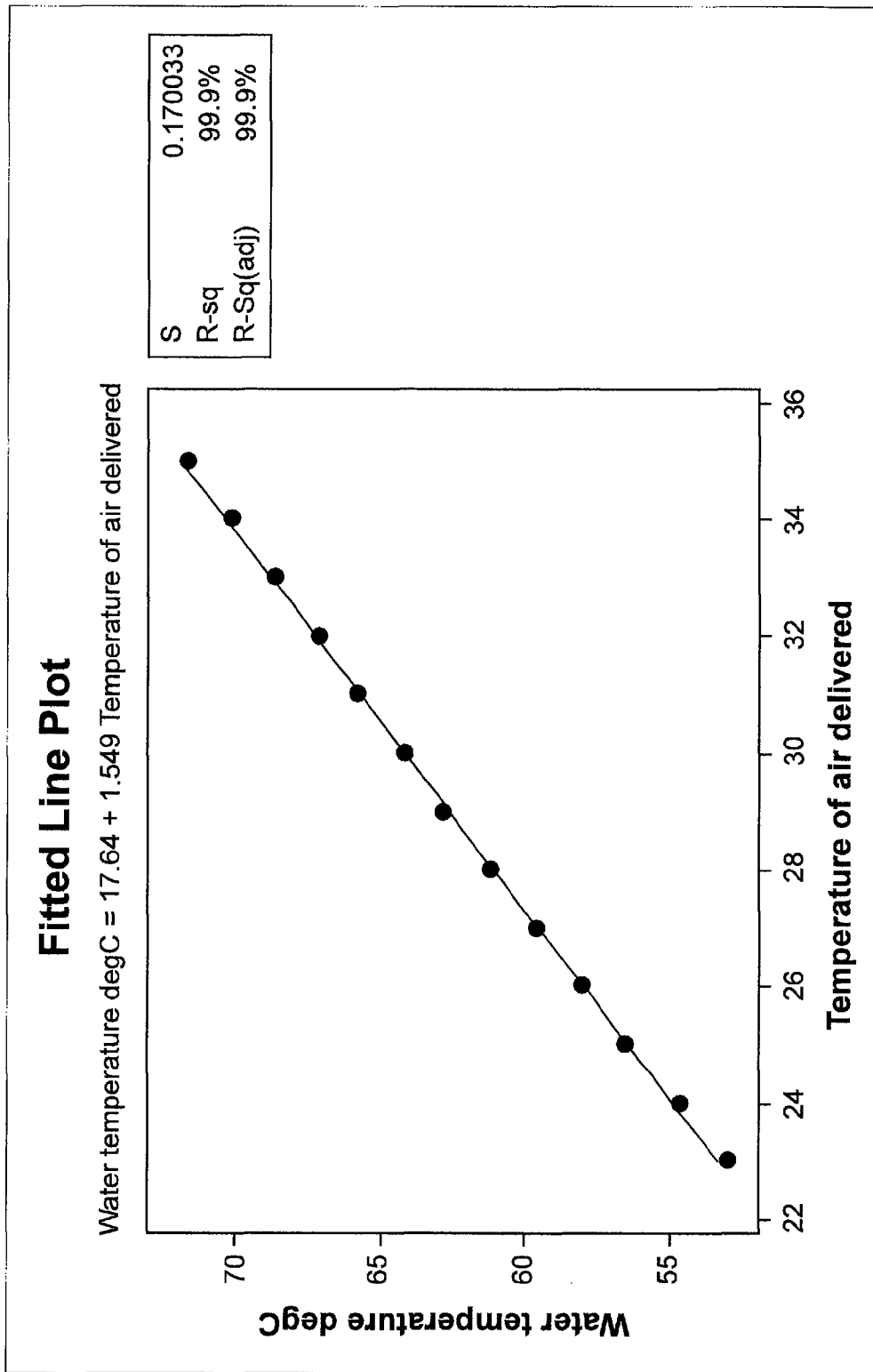
FIG. 10 schematically depicts a change in water temperature in response to a change in delivered gas temperature according to another example.

Referring to Table 3 and FIG. 10, in this example, the system of FIG. 6 is controlled to deliver saturated air and the temperature at the patient interface is changed.

TABLE 2

| Water temperature deg C. | Air temperature deg C. | Air absolute humidity (mg/L) | Air relative humidity | Humidification output mg/L | Temperature of air delivered | Humidity of air delivered (mg/L) | Humidity of air delivered % RH |
|---|---|---|---|---|---|---|---|
| 38.5 | 15 | 10 | 80% | 2.5 | 15 | 12.5 | 100% |
| 40.2 | 16 | 10 | 75% | 3.3 | 16 | 13.3 | 100% |
| 42 | 17 | 10 | 71% | 4.1 | 17 | 14.1 | 100% |
| 44 | 18 | 10 | 66% | 5.1 | 18 | 15.1 | 100% |
| 46 | 19 | 10 | 62% | 6.2 | 19 | 16.2 | 100% |
| 47.8 | 20 | 10 | 58% | 7.2 | 20 | 17.2 | 100% |
| 49.5 | 21 | 10 | 55% | 8.3 | 21 | 18.3 | 100% |
| 51.2 | 22 | 10 | 52% | 9.4 | 22 | 19.4 | 100% |
| 53 | 23 | 10 | 48% | 10.6 | 23 | 20.6 | 100% |
| 54.8 | 24 | 10 | 46% | 12.0 | 24 | 22.0 | 100% |
| 56.5 | 25 | 10 | 43% | 13.3 | 25 | 23.3 | 100% |
| 58 | 26 | 10 | 41% | 14.5 | 26 | 24.5 | 100% |
| 59.8 | 27 | 10 | 38% | 16.1 | 27 | 26.1 | 100% |
| 61.5 | 28 | 10 | 36% | 17.7 | 28 | 27.7 | 100% |
| 63 | 29 | 10 | 34% | 19.2 | 29 | 29.2 | 100% |
| 64.5 | 30 | 10 | 32% | 20.7 | 30 | 30.7 | 100% |

TABLE 3

| Water temperature deg C. | Air temperature deg C. | Air absolute humidity (mg/L) | Air relative humidity | Humidification output mg/L | Temperature of air delivered | Humidity of air delivered (mg/L) | Humidity of air delivered % RH |
|---|---|---|---|---|---|---|---|
| 53 | 22.5 | 10 | 50% | 10.6 | 23 | 20.6 | 100% |
| 54.6 | 22.5 | 10 | 50% | 11.8 | 24 | 21.8 | 100% |
| 56.5 | 22.5 | 10 | 50% | 13.4 | 25 | 23.4 | 100% |
| 58 | 22.5 | 10 | 50% | 14.6 | 26 | 24.6 | 100% |
| 59.6 | 22.5 | 10 | 50% | 16.1 | 27 | 26.1 | 100% |
| 61.2 | 22.5 | 10 | 50% | 17.6 | 28 | 27.6 | 100% |
| 62.8 | 22.5 | 10 | 50% | 19.3 | 29 | 29.3 | 100% |
| 64.2 | 22.5 | 10 | 50% | 20.8 | 30 | 30.8 | 100% |
| 65.8 | 22.5 | 10 | 50% | 22.6 | 31 | 32.6 | 100% |
| 67.2 | 22.5 | 10 | 50% | 24.2 | 32 | 34.2 | 100% |
| 68.7 | 22.5 | 10 | 50% | 26.1 | 33 | 36.1 | 100% |
| 70.2 | 22.5 | 10 | 50% | 28.0 | 34 | 38.0 | 100% |
| 71.7 | 22.5 | 10 | 50% | 30.0 | 35 | 40.0 | 100% |

The ambient air is assumed to be 22.5° C., the absolute humidity is 10 mg/L, and the relative humidity is 50%. The ambient air conditions are assumed not to change. The temperature of the water in the humidifier tub is adjusted to achieve 100% RH at the patient interface, as shown in Table 3. As the requested temperature at the patient interface is increased, the temperature of the water in the humidifier tub is increased to maintain saturation of the air delivered. As shown in FIG. 10, the relationship between the temperature of the water in the humidifier tub and the temperature of the air delivered is approximately linear, e.g. there is approximately an increase of 1.55° C. in the water temperature for each 1° C. increase in the temperature of the air delivered to the patient interface. The temperature at the mask may be automatically and independently controlled by controlling the power to the heated tube.

In this example, the temperature of the air delivered to the patient interface may be selected by the patient, or clinician, through the use of, for example, the control buttons 14 of the flow generator 2. The patient may select an operation mode that permits adjustment of the temperature of the air at the patient interface. The heating element of the humidifier is then automatically controlled to increase the temperature of the water in the humidifier tub as the requested temperature of the air at the patient interface is increased, and correspondingly decrease the water temperature as the requested air temperature decreases.

EXAMPLE 3

Adjustment to Change in Ambient Humidity

Figure 11:
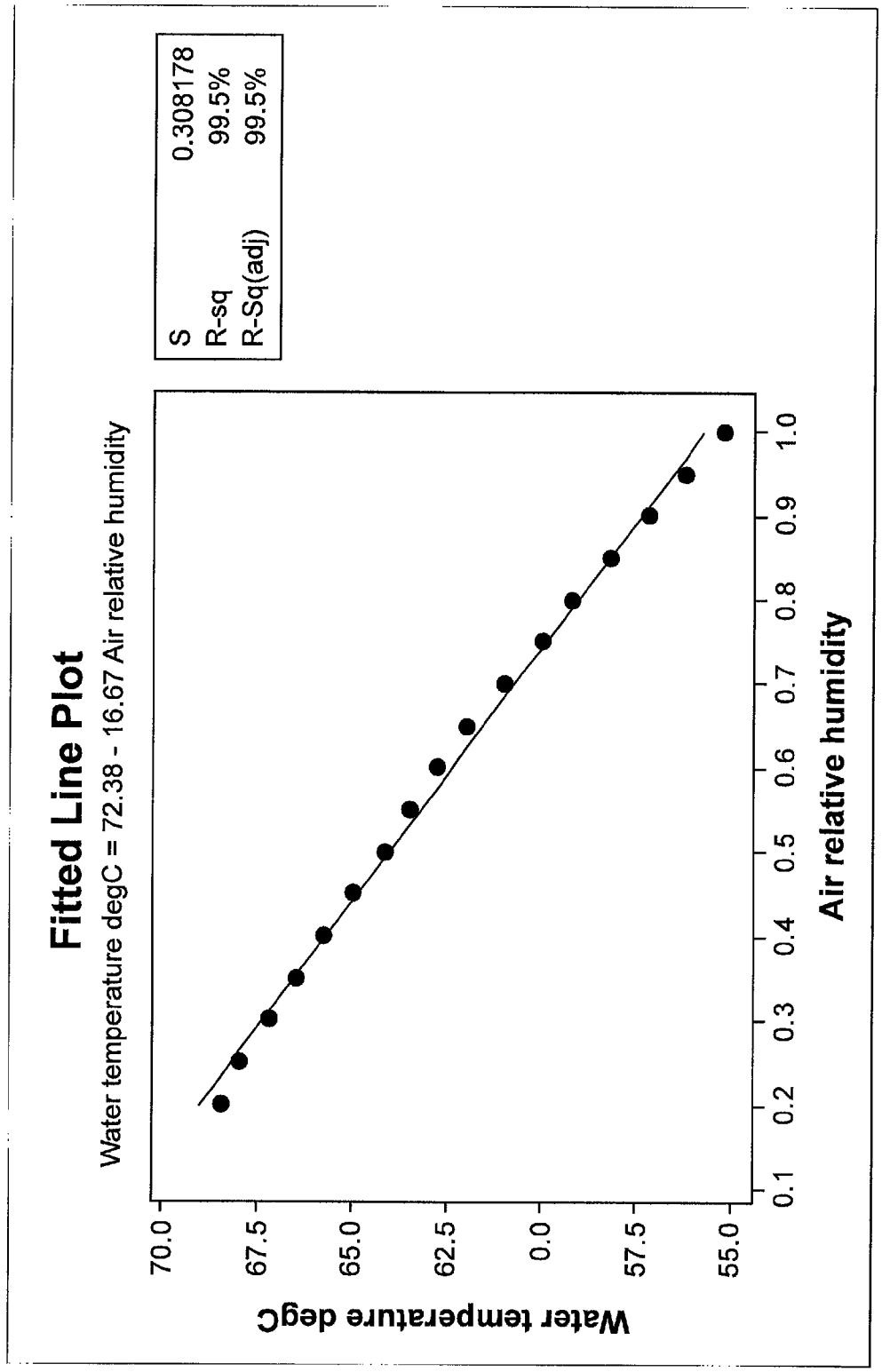
FIG. 11 schematically depicts a change in water temperature in response to a change in ambient humidity where there is no change in ambient temperature according to another example.

The system of FIG. 6 may also be configured to adjust for changes in ambient humidity. For example, signals from the sensors 50, 52 may be provided to the controller(s) 40 and/or 44 to periodically or continuously calculate the absolute humidity of the ambient air. As shown in Table 4 and FIG. 11, the temperature of the ambient air is maintained relatively constant, for example 22.5° C., but the absolute humidity changes throughout the course of the patient's sleep cycle.

TABLE 4

| Water temperature deg C. | Air temperature deg C. | Air absolute humidity (mg/L) | Air relative humidity | Humidification output mg/L | Temperature of air delivered | Humidity of air delivered (mg/L) | Humidity of air delivered % RH |
|---|---|---|---|---|---|---|---|
| 68.5 | 22.5 | 4 | 20% | 26.8 | 30 | 30.8 | 100% |
| 68 | 22.5 | 5 | 25% | 26.0 | 30 | 31.0 | 100% |
| 67.2 | 22.5 | 6 | 30% | 24.9 | 30 | 30.9 | 100% |
| 66.5 | 22.5 | 7 | 35% | 23.9 | 30 | 30.9 | 100% |
| 65.8 | 22.5 | 8 | 40% | 22.9 | 30 | 30.9 | 100% |
| 65 | 22.5 | 9 | 45% | 21.8 | 30 | 30.8 | 100% |
| 64.2 | 22.5 | 10 | 50% | 20.8 | 30 | 30.8 | 100% |
| 63.5 | 22.5 | 11 | 55% | 19.9 | 30 | 30.9 | 100% |
| 62.8 | 22.5 | 12 | 60% | 19.0 | 30 | 31.0 | 100% |
| 62 | 22.5 | 13 | 65% | 18.0 | 30 | 31.0 | 100% |
| 61 | 22.5 | 14 | 70% | 16.9 | 30 | 30.9 | 100% |
| 60 | 22.5 | 15 | 75% | 15.8 | 30 | 30.8 | 100% |
| 59.2 | 22.5 | 16 | 80% | 14.9 | 30 | 30.9 | 100% |
| 58.2 | 22.5 | 17 | 85% | 13.8 | 30 | 30.8 | 100% |
| 57.2 | 22.5 | 18 | 90% | 12.8 | 30 | 30.8 | 100% |
| 56.2 | 22.5 | 19 | 95% | 11.9 | 30 | 30.9 | 100% |
| 55.2 | 22.5 | 20 | 100% | 11.0 | 30 | 31.0 | 100% |

The temperature of the water in the humidifier tub is adjusted to achieve 100% RH at the patient interface. The temperature at the patient interface is maintained constant, for example 30° C. The temperature of the water in the humidifier tub is thus decreased as the ambient air absolute humidity, and relative humidity, increases. Control of the system in this manner permits the temperature of saturated air to be delivered to the patient interface to be maintained relatively constant, as shown in Table 4.

EXAMPLE 4

Adjustment to Change in Air Flow Rate

Figure 12:
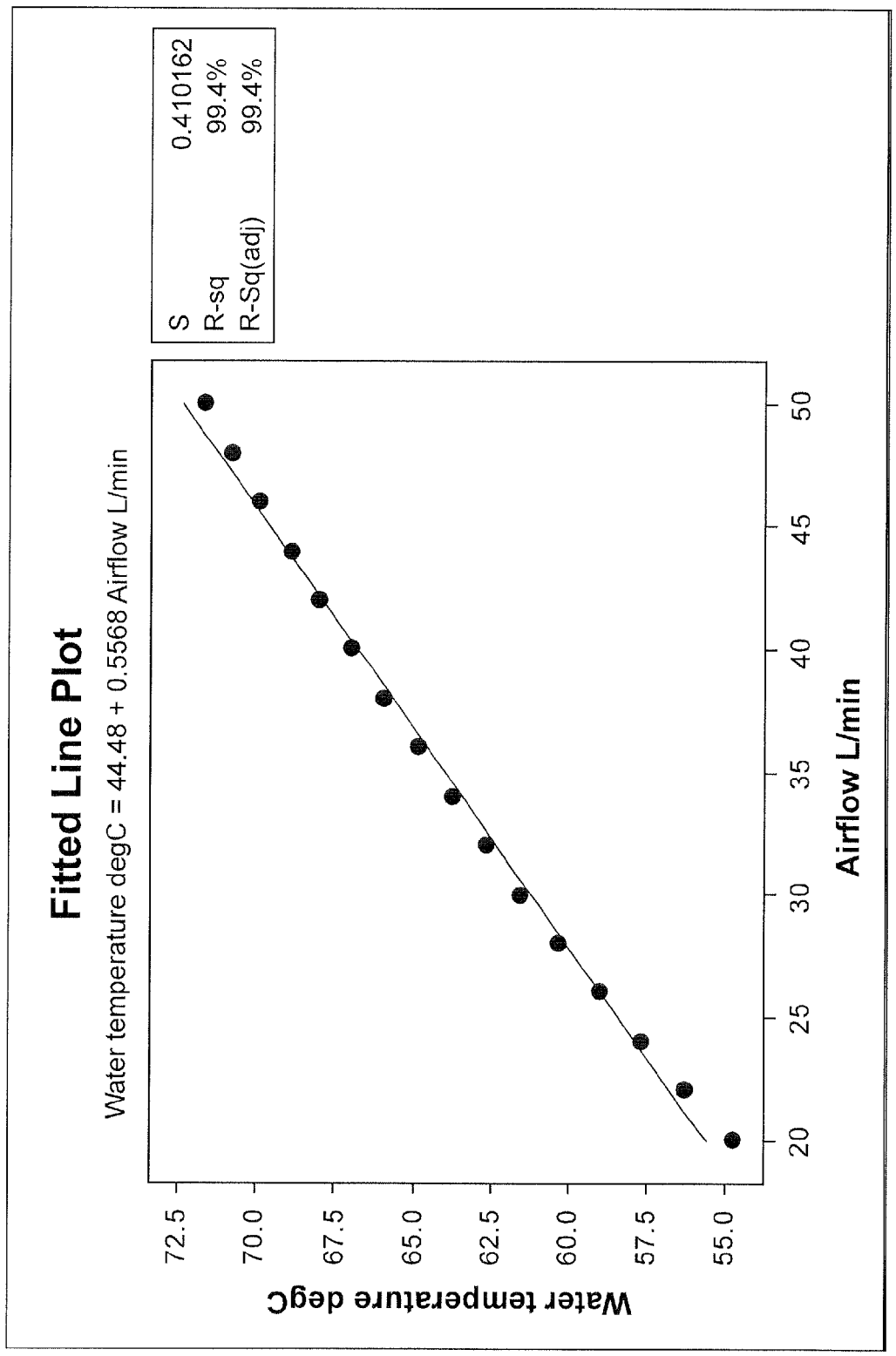
FIG. 12 schematically depicts a change in water temperature in response to a change in the average gas flow rate through the humidifier according to one example.

Referring to Table 5 and FIG. 12, the ambient temperature and relative humidity and the temperature of the air delivered to the patient interface are constant.

TABLE 5

| Water temperature deg C. | Air temperature deg C. | Air absolute humidity (mg/L) | Air relative humidity | Humidification output mg/L | Temperature of air delivered | Airflow L/min | Humidity of air delivered (mg/L) | Humidity of air delivered % RH |
|---|---|---|---|---|---|---|---|---|
| 54.8 | 22.5 | 10 | 50% | 21.0 | 30 | 20 | 31.0 | 100% |
| 56.3 | 22.5 | 10 | 50% | 21.0 | 30 | 22 | 31.0 | 100% |
| 57.7 | 22.5 | 10 | 50% | 21.0 | 30 | 24 | 31.0 | 100% |
| 59 | 22.5 | 10 | 50% | 20.9 | 30 | 26 | 30.9 | 100% |
| 60.3 | 22.5 | 10 | 50% | 21.0 | 30 | 28 | 31.0 | 100% |
| 61.6 | 22.5 | 10 | 50% | 21.1 | 30 | 30 | 31.1 | 100% |
| 62.7 | 22.5 | 10 | 50% | 21.0 | 30 | 32 | 31.0 | 100% |
| 63.8 | 22.5 | 10 | 50% | 20.9 | 30 | 34 | 30.9 | 100% |
| 64.9 | 22.5 | 10 | 50% | 21.0 | 30 | 36 | 31.0 | 100% |
| 66 | 22.5 | 10 | 50% | 21.0 | 30 | 38 | 31.0 | 100% |
| 67 | 22.5 | 10 | 50% | 21.0 | 30 | 40 | 31.0 | 100% |
| 68 | 22.5 | 10 | 50% | 21.0 | 30 | 42 | 31.0 | 100% |
| 68.9 | 22.5 | 10 | 50% | 20.9 | 30 | 44 | 30.9 | 100% |
| 69.9 | 22.5 | 10 | 50% | 21.0 | 30 | 46 | 31.0 | 100% |
| 70.8 | 22.5 | 10 | 50% | 21.0 | 30 | 48 | 31.0 | 100% |
| 71.7 | 22.5 | 10 | 50% | 21.0 | 30 | 50 | 31.0 | 100% |

The flow rate through the humidifier is adjusted, for example through the action of ResMed's AUTOSET® control algorithm. The flow rate may also be adjusted, for example, in response to a leak at the patient interface. As shown in Table 5 and FIG. 12, the temperature of the water in the humidifier tub is increased as the air flow rate increases to maintain saturation at the patient interface.

The respiratory system may be controlled according to each of Examples 1-4 and combinations thereof. The data provided in Tables 1 and 3-5 and FIGS. 8 and 10-12 maybe stored in a memory, for example in controller(s) 40 and/or 44. The controllers 40, 44 may be programmed to look up data from the stored information. The controllers 40, 44 may also be programmed to interpolate and/or extrapolate data from the stored information. The setpoint of the heating element that provides the appropriate evaporation rate for each combination of ambient temperature and humidity, flow and predetermined output humidity may be determined experimentally to characterize the design and then built into the controller, for example stored as a table in a memory or as a set of equations.

Although the relative humidity of the air delivered to the patient interface in each of Examples 1-4 is described as 100%, it should be appreciated that the relative humidity of the air delivered to the patient interface may be about 50%-100%, for example about 70%-90%, or about 80% as another example, or any other value selected by the patient or clinician.

Humidifier Control

The humidifier 4 may provide a user selectable setting that will provide an automatic delivery of a predetermined moisture content at the mask 32. An example value for delivered air moisture content is determined taking into account the conditions which lead to unwanted condensation in the tube 30. For users with normal upper airways a desired physiological outcome is to condition the air to approximate normal inspiratory conditions at the nose. For example, the ambient air may be 20° C. and 25% RH (4 mg/L AH). The air may be heated and humidified to conditions equivalent to about 20° C. at 80% RH (14 mg/L AH). A moisture content of 14 mg/L, which corresponds to the absolute humidity at 20° C. at 80% RH, may therefore be chosen to be the example value. The humidifier would be set to hold the output to 14 mg/L. The difference of 10 mg/L would be added by the humidifier. It should be appreciated that although this value may be chosen as the example value, and the humidifier may be configured to include a user setting that automatically provides this value, the example value may be determined, or revised, on the basis of clinical advice and the humidifier may be configured, or reconfigured, to include a user setting that automatically provides a clinically determined moisture content. For example, the patient or clinician may select an absolute humidity from about 10 mg/L-25 mg/L, for example 20 mg/L which corresponds generally to a relative humidity between 70%-80% at a temperature of approximately 27°-28° C.

The actual temperature of delivered air in a CPAP system may be higher than room ambient temperature, typically about 29° C., in the case of a respiratory apparatus provided with heated tubing. Therefore, the RH value at the nose would be less than 50% for the same absolute humidity value. In the case of a respiratory apparatus without heated tubing, the humidified air cools in the tubing to one or two degrees above ambient. Without heated tubing, the air would be delivered at about 22° C. and 70% RH (14 mg/L AH).

At the optimum setting, e.g. 10 mg/L, condensation in the breathing tube will not occur unless the room temperature falls sufficiently to cause the temperature of the delivered air to fall below its dew point (being approximately 16° C. for air at 29° C. as typically delivered to the mask with a CPAP apparatus operating in 22° C. ambient). Should the room temperature continue to drop, causing the delivered air temperature to also drop, then the heater temperature is automatically reduced to lower the delivered moisture content below the optimum level in order to avoid condensation, but still to target the optimum level as closely as possible.

Figure 13:
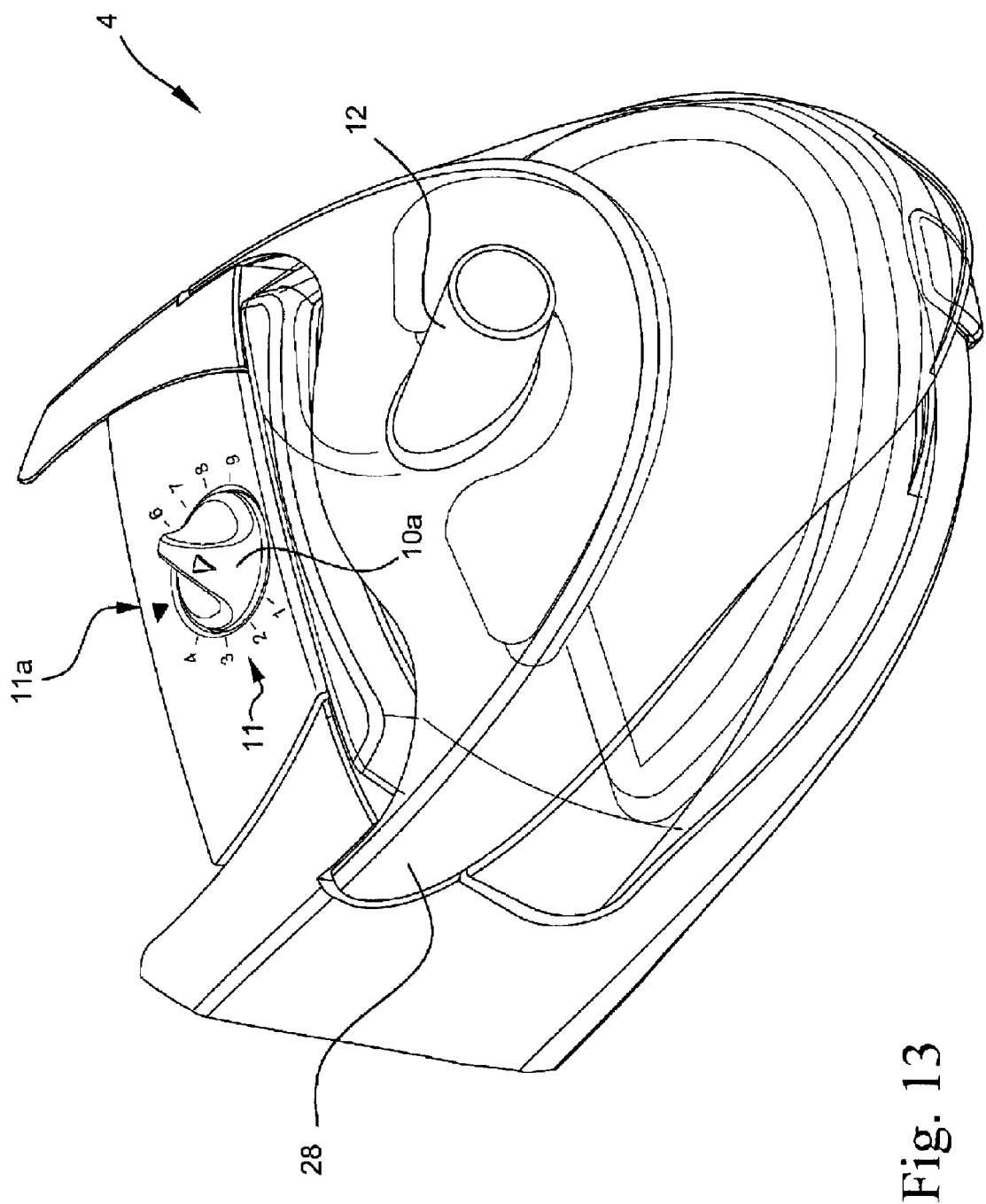
FIG. 13 schematically depicts a humidifier according to another sample embodiment.

Referring to FIG. 13, a humidifier 4 according to another sample embodiment of the invention comprises a control knob 10 including a setting indicator 10. The humidifier 4 comprises indicia 11 that indicate a plurality of settings. An indicia 11*a* may designate the automatic setting that provides the default moisture content. For example, as shown in FIG. 13, the automatic setting indicia 11*a* may comprise, for example, a ▼. It should be appreciated that any other indicia may be used, for example the indicia 11a may include the words "optimum" or "automatic." The remaining indicia 11 may comprise numbers, for example 1-4 and 6-9, that permit the user to increase and decrease the delivered humidity. The indicia may also be configured to show values for the relative or absolute humidity and temperature, for example as percentage RH. To select the default setting, the user aligns the setting indicator 10a of the control knob 10 with the automatic setting indicium 11a. To adjust the humidity setting, the user aligns the setting indicator 10a with any of the other indicia 11, or at any position between any of the other indicia 11. For example, to lower the humidity setting, the user may align the setting indicator 10a with any one of the numbers 1-4, or any setting therebetween. Similarly, to increase the humidity setting, the user may align the setting indicator 10a to any one of the numbers 6-9, or any setting therebetween. It should also be appreciated that the control may be other than a knob, for example the control may include a display, such as an LCD, to display the setting, and a button, or buttons, to permit selection of the setting, or to change the displayed setting.

Figure 14:
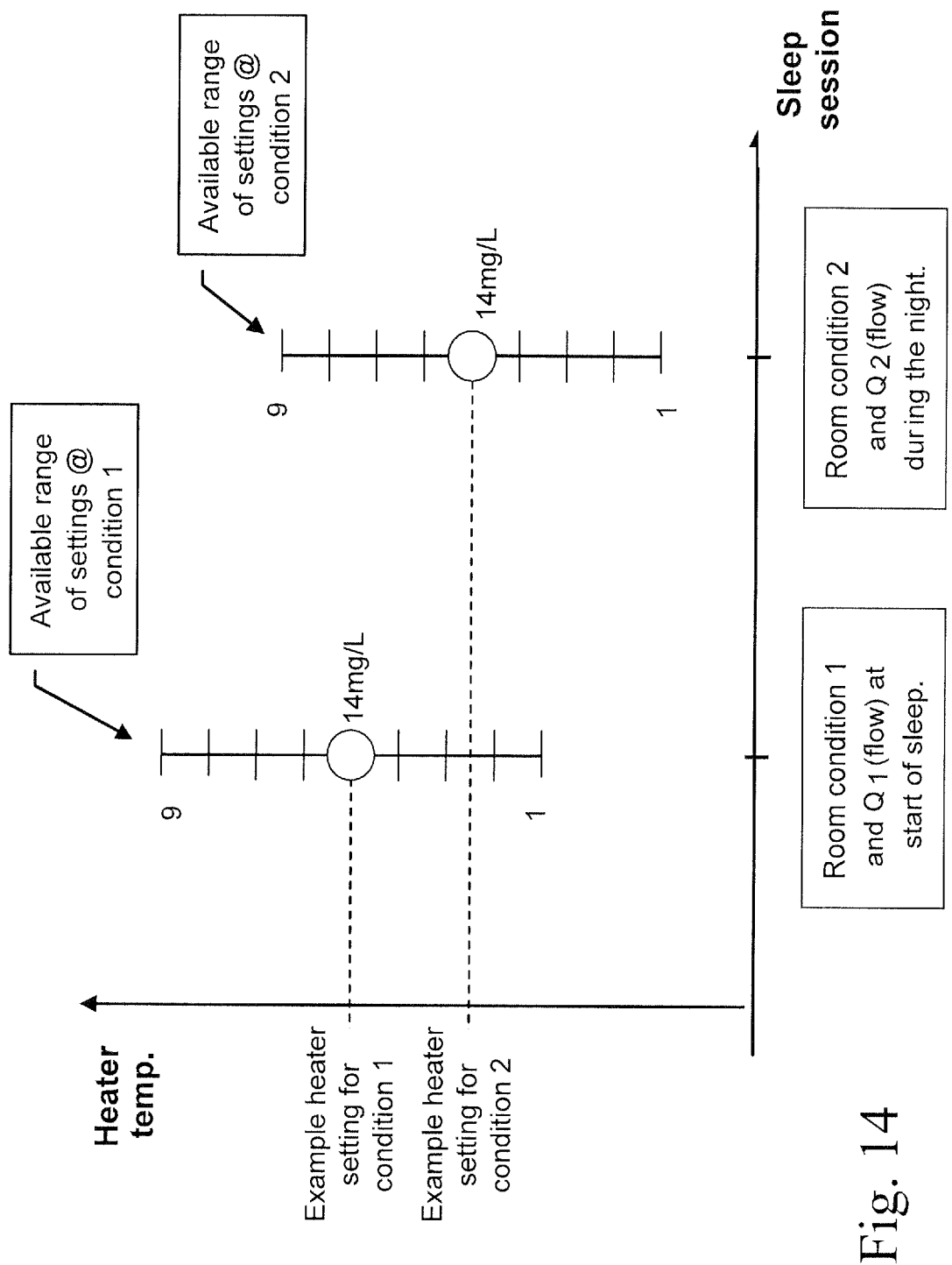
FIG. 14 schematically depicts compensation of an example setting of the humidifier by controlling the heating element of the humidifier in responses to changes in ambient conditions and/or mean flow rate during use of the respiratory apparatus according to a sample embodiment.

As shown in FIG. 14, when the automatic default moisture content is selected, i.e. by aligning the setting indicator 10a with the indicia 11a, the humidifier 4 may be controlled so that the heating element 46 of the humidifier 4 is continuously adjusted to maintain the moisture content of the flow of breathable gas at the predetermined default level, e.g. 14 mg/L. As discussed in more detail below, the heating element 46 is continuously adjusted to maintain the moisture content of the flow to a value as close to the default level as possible while still preventing condensation, or rain-out, in the tube 30.

In response to changing room conditions during the user's sleep session, e.g. ambient temperature, ambient relative humidity, and/or ambient pressure, and/or in response to changes in the flow, the heating element 46 is controlled to maintain the default moisture content, e.g. 14 mg/L. For example, at the start of the patient's sleep session (condition 1), the room conditions may be at a first temperature, a first relative humidity and a first pressure. The flow generator may produce a first flow Q1 at the start of the patient's sleep session. The heating element 46 of the humidifier 4 is controlled so that the default moisture content, e.g. 14 mg/L, is provided when the patient selects the automatic setting by aligning the setting indicator 10a with the indicia 11a.

Although condition 1 is described above as corresponding to the start of the patient's sleep session, it should be appreciated that condition 1 may correspond to a time from start up of the respiratory system, for example a warm-up time that takes into account the effect of the delivered air temperature above the ambient temperature.

During the course of the patient's sleep session, room conditions, including the ambient temperature, ambient relative humidity, and/or pressure, may change to a second condition (condition 2). The flow Q2 generated by the flow generator may also change during the course of the patient's sleep session. The heating element 46 of the humidifier 4 is controlled so that the moisture content of the flow is the default content, e.g. 14 mg/L at condition 2, regardless of the change in the room conditions.

Similarly, if the patient chooses a different setting at start up (condition 1), for example by aligning the setting indicator 10a with the indicia "9" (to increase the moisture content from default) or the indicia "1" (to decrease the moisture content from default), the heating element 46 is controlled so that the moisture content that is delivered to the mask is the same at condition 2 as is delivered at condition 1. The full range of moisture content settings, which is centered about the default setting, is continuously and automatically re-scaled in response to the monitored values of the ambient temperature, ambient relative humidity, ambient pressure, and delivered flow so that the selected setting is always calibrated to deliver the selected moisture content.

Humidity Control First Embodiment

Figure 15:
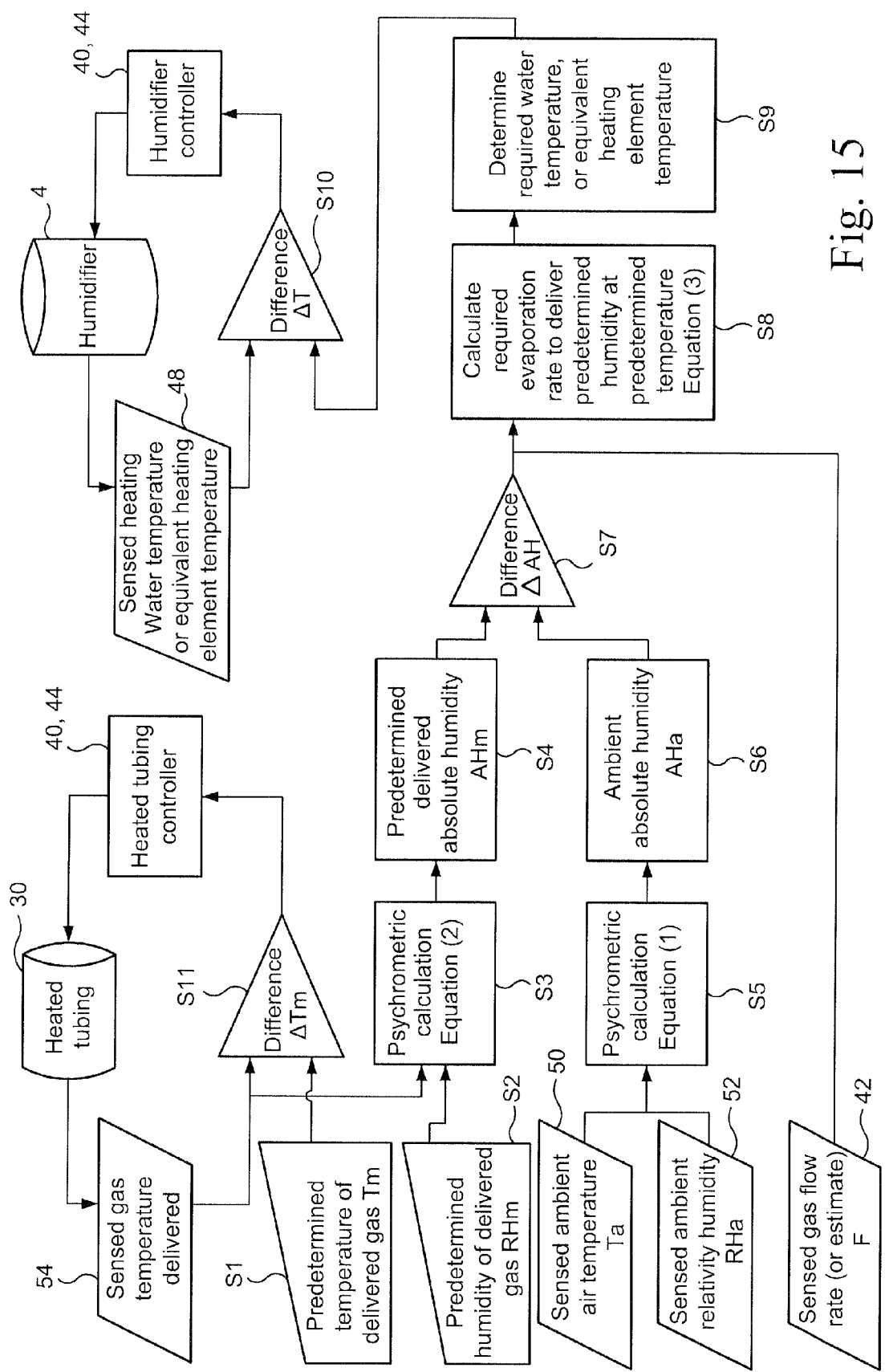
FIG. 15 schematically depicts a control of the respiratory apparatus according to a sample embodiment.

Referring to FIG. 15, a control system and process for the respiratory apparatus is illustrated. At S1, a temperature Tm of the flow to be delivered to the mask is determined. At S2, a relative humidity RHm of the flow to be delivered to the mask is determined. It should be appreciated that the user may set the temperature Tm and the relative humidity RHm, for example by using the buttons 14 on the flow generator 2. Alternatively, the user may select a moisture content, i.e. absolute humidity, of the flow to be delivered to the mask by adjusting the control knob 10 of the humidifier. For example, the user may align the setting indicator 10a to the default setting indicia 11a. The default moisture content may be a nominal moisture content, e.g. 14 mg/L, or a clinically determined moisture content. The user may also select a moisture content other than the default by aligning the setting indicator 10a with another of the indicia 11. In the case where the humidifier is integrally connected to the flow generator, the respiratory apparatus may be configured to permit the user to select the moisture content using either the buttons 14 of the flow generator 2 or the control knob 10 of the humidifier 4. In the case where the user selects a moisture content, the temperature Tm and the relative humidity RHm to be delivered to the mask correspond to the selected moisture content setting.

The heating element of the air delivery tube 30 is controlled to provide the predetermined temperature Tm to the flow delivered to the mask. The temperature sensor 54 at the end of the air delivery hose 30 senses the actual temperature of the flow at the end of the air delivery hose 30. The difference ΔTm between the predetermined temperature Tm and the sensed temperature is determined in S11 by the controller(s) 40, 44 and the controller(s) 40, 44 adjusts the power to the heating element of the air delivery tube 30 until the difference between the predetermined temperature and the sensed temperature is substantially zero.

At S3, the temperature sensed by the sensor 54 and the predetermined relative humidity RHm to be delivered to the mask are inserted into equation (2) to provide the absolute humidity AHm, i.e. moisture content, to be delivered to the mask at S4. At S5, the ambient temperature Ta from the sensor 50 and the ambient relative humidity RHa from the sensor 5 are inserted into equation (1) to provide the ambient absolute humidity AHa at S6. At S7, the difference ΔAH between the absolute humidity AHm to be delivered to the mask and the ambient absolute humidity AHa is determined. The difference ΔAH is the absolute humidity that the humidifier 4 must add to the flow in order to deliver the selected moisture content.

At S8, the flow rate F as sensed by the flow sensor 42, or estimated, is inserted into equation (3) along with the difference ΔAH to determine the required evaporation rate E from the supply of water in the humidifier. At S9, the required water temperature, or equivalent temperature of the humidifier heating element 46, to produce the evaporation rate E is determined, for example by the closed-loop control discussed above.

At S10, the difference ΔT between the water temperature as sensed by the sensor 48 and the required water temperature determined at S9 is calculated. The controller(s) 40, 44 controls the heating element 46 of the humidifier 4 until the difference between the required water temperature and the sensed water temperature is substantially zero. Alternatively, the heating element 46 is controlled until the difference between the required heating element temperature and the sensed heating element temperature is substantially zero.

Humidity Control Second Embodiment

Figure 16:
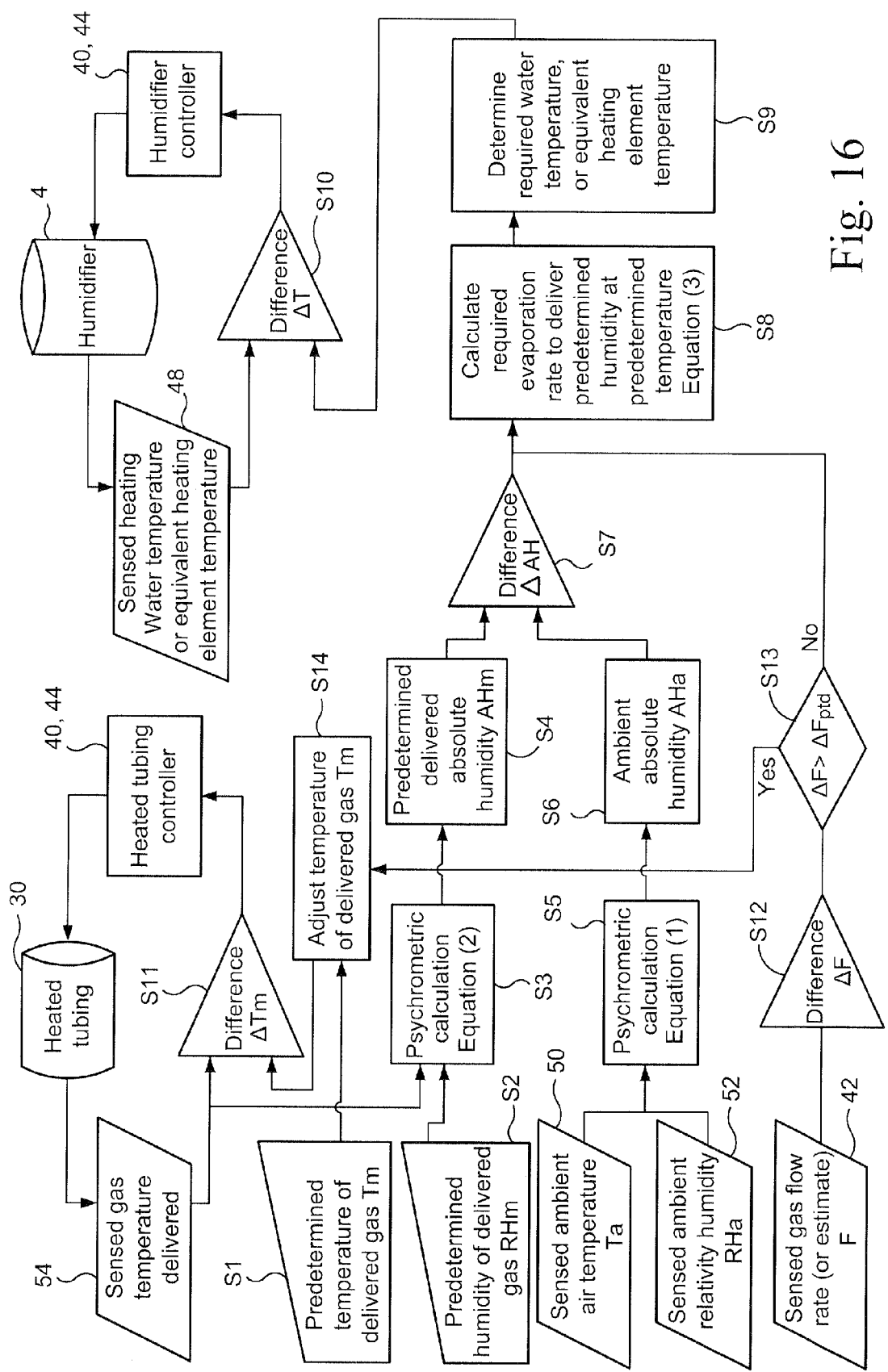
FIG. 16 schematically depicts a control of the respiratory apparatus according to another sample embodiment.

Referring to FIG. 16, a control system and process for the respiratory apparatus according to another sample embodiment is illustrated. During use of the respiratory system, the flow rate may change, for example through the action of the AUTOSET® control algorithm, which may provide a relatively slow change in the flow rate, or due to the development of leaks, either around the mask cushion or mouth leak from the use of a nasal mask, which may provide a relatively fast change in the flow rate. If the flow rate changes rapidly, the control of the heated tubing or hose and/or humidifier may not respond rapidly enough to prevent condensation in the tubing as the response is relatively slow because it takes a relatively longer time for the humidifier to change the temperature of the supply of water.

As shown in FIG. 16, a change, or difference, $\Delta F$ in the flow rate sensed by the flow rate sensor 42, or for example estimated from the blower speed, is determined at S12. The difference $\Delta F$ may be determined by comparing the sensed, or estimated, flow rate at periodic intervals. At S13, the difference $\Delta F$ is compared to a predetermined difference $\Delta F_{ptd}$. If the difference $\Delta F$ between periodic flow rates exceeds a predetermined amount $\Delta F_{ptd}$, the process proceeds to S14 and the temperature Tm of the gas delivered to the patient interface is adjusted, for example by controlling the heated tubing 30 using the controller(s) 40, 44. If the difference $\Delta F$ does not exceed the predetermined amount $\Delta F_{ptd}$, the process proceeds similar to that described above with respect to the first embodiment and the required evaporation rate is calculated in S8 from the absolute humidity difference $\Delta AH$ and the detected, or estimated, flow rate.

If the difference $\Delta F$ is negative, i.e. the change in the flow rate is a decrease, the temperature Tm is increased in S14. The temperature Tm may be increased in S14 sufficiently to keep the temperature Tm of the air delivered to the patient interface above the saturation point. The decrease in flow rate also results in a decrease of the water temperature or the heating element temperature in S9, a calculation of the difference $\Delta T$ in S10, and control of the heating element by the controller(s) 40, 44 to reduce the temperature setpoint of the humidifier. As the temperature of the water supply of the humidifier is reduced, there is a margin for the absolute humidity AHm to overshoot without reaching the saturation point.

The difference $\Delta Tm$ between the temperature sensed by the temperature sensor 54 and the adjusted temperature Tm is determined in S11 and the heated tubing 30 is controlled until the difference $\Delta Tm$ is substantially zero. Over a predetermined time period, the adjusted temperature Tm in S12 is gradually reduced until the temperature of the water supply in the humidifier is reduced to the new setpoint of the humidifier.

If the flow rate difference $\Delta F$ determined in S11 is positive, i.e. the change in flow rate is an increase, and greater than the predetermined difference $\Delta F_{ptd}$, the adjustment in S14 may be a reduction of the temperature Tm to keep the absolute humidity AHm close to saturation. However, the patient may find the reduction of the temperature Tm to be uncomfortable. In that case, the controller(s) 40, 44 may be configured to disregard a flow rate difference $\Delta F$ that indicates an increase in the flow rate.

The humidifier and respiratory apparatus discussed herein with respect to the sample embodiments provide inexperienced or new users of heated humidifiers with an automatic, or default, setting that is designed to provide the default moisture content in the delivered air (nominally 14 mg/L) for any given use conditions. During the patient's sleep session, automatic compensation will be invoked to reduce the target value of the default moisture content, if necessary, to avoid condensation from occurring in the air tube.

Correct performance of the humidifiers according to the sample embodiments disclosed herein does not require any user knowledge or intervention in order to properly set up and operate the device. This benefits users who otherwise find it difficult to establish a suitable humidifier setting. Correct performance is automatically maintained during the patient's sleep session, responding to changes to the factors influencing the delivered air moisture content, and the potential for condensation), these factors including ambient absolute humidity, ambient temperature, relative humidity and pressure, and delivered air flow rate.

The user is provided with additional settings to fine-tune the automatic, or default, setting, if necessary, according to their preference. The full-scale range of available settings is continuously re-scaled to maintain the centered value to be calibrated at the default moisture content, subject to the prevention of condensation in the air delivery hose as discussed above. This means that, unlike prior art humidifiers, the default setting and the available full-scale range of settings is always calibrated to actual ambient conditions. Climate differences in one region, e.g. cold wet climate, does not compromise the available humidification performance or available settings in another region as can be the case in devices with fixed heater settings.

For example, the user may determine that a setting lower than the default or automatic setting, such as "3" as marked by indicia 11, or a setting higher than the default or automatic setting, such as "7" as marked by indicia 11, provides the most comfortable humidified flow. The user may therefore select the desired setting and the absolute humidity of the flow delivered to the patient interface will be the most comfortable, as determined by the patient, regardless of the ambient conditions and/or flow rate.

Humidifier Control Third Embodiment

Figure 17:
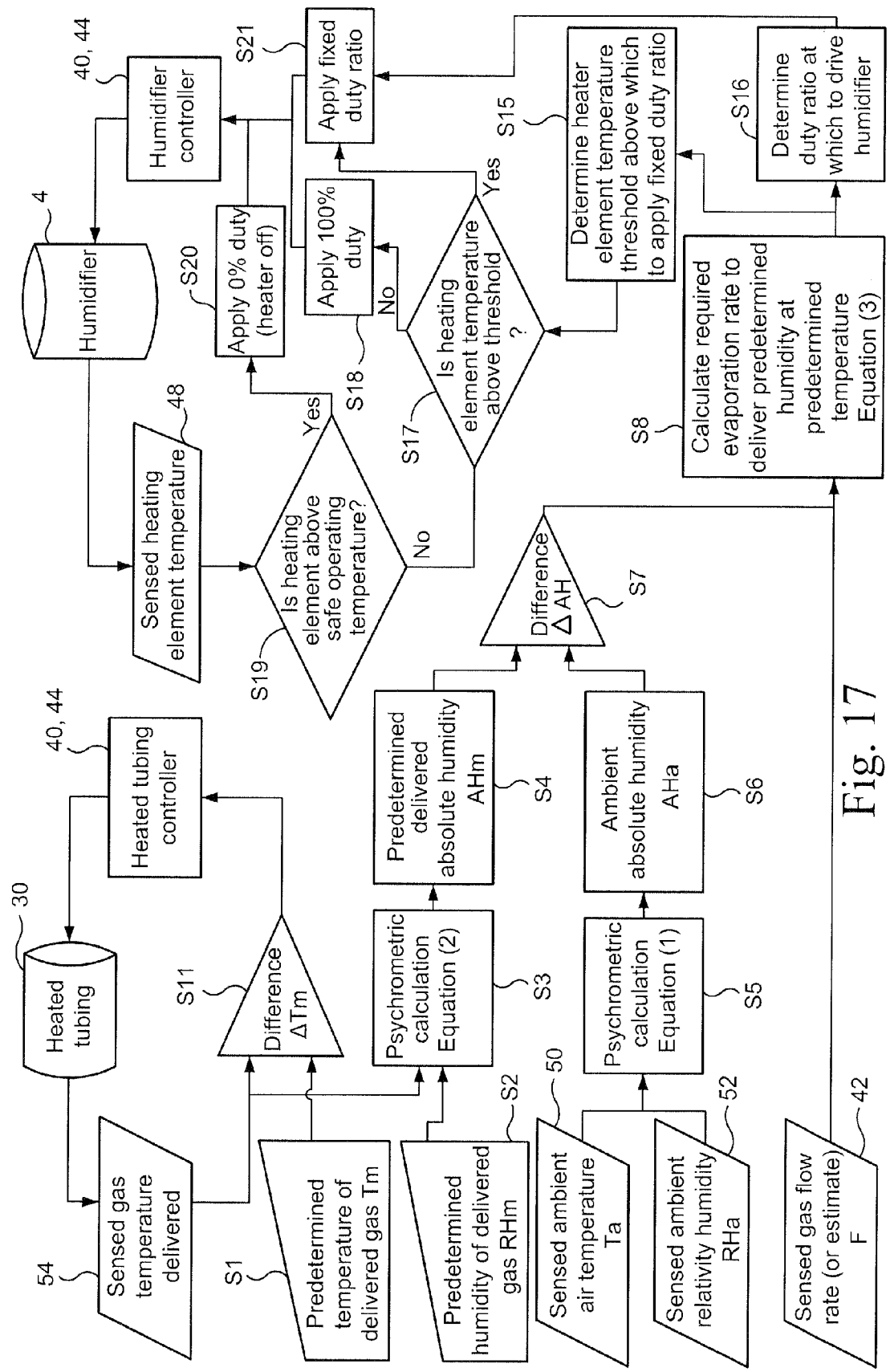
FIG. 17 schematically depicts a control of the respiratory apparatus according to another sample embodiment.

Referring to FIG. 17, a control system and process for the respiratory apparatus according to another sample embodiment is illustrated. The system and process of the sample embodiment of FIG. 17 operates similar to the sample embodiment of FIG. 15 for S1-S8 and S11 as described above.

After calculating the required evaporation rate to deliver the predetermined humidity at the predetermined temperature in S8, a heater element temperature threshold above which to apply a fixed duty ratio is determined in S15 and a duty ratio at which to drive the humidifier is determined in S16. After determining the heater element temperature threshold in S15, a determination is made in S17 whether the heating element temperature is above the threshold. If the heating element temperature is above the threshold (S17: Yes), a fixed duty ratio is applied to the heating element in S21. If the heating element temperature is not above the threshold (S17: No), a duty ratio of 100% is applied to the heating element in S18.

A determination is made in S19 if the heating element temperature, as sensed by the heating element temperature sensor 48, is above a safe operating temperature. If the sensed heating element temperature is below the safe operating temperature (S19: No), the heating element temperature is checked again in S17 to determine if the heating element temperature is above the threshold. If the sensed heating element temperature is above the safe operating temperature (S19: Yes), the duty cycle of the heating element is set to 0%, i.e. the heating element is turned off, in S20.

A humidifier may be configured to operate using different types of containers, or tubs, to contain the water supply. One such humidifier is disclosed, for example, in U.S. Application 61/097,765, filed Sep. 17, 2008, the entire contents of which are incorporated herein by reference. Two types of humidifier tub which may be used are a "reusable" tub with, for example, a stainless steel base, and a "disposable" tub with, for example, an aluminium base. The thermal transfer properties differ in the two bases. When the heating element is regulated to a constant temperature, the two tubs may provide different humidity outputs. However, it is desirable that the humidity output be predictable no matter which tub is fitted to the device. This is also preferable when there is means to detect which type of tub is fitted in the humidifier.

The humidity output may be correlated to the duty ratio at which the heating element is powered, rather than the temperature at which it is held, as described above with reference to FIG. 17. This is because at constant duty ratio the heater element is delivered power at a constant rate, and the main dissipation of that power in the system is through evaporation of water from the tub. In practice, the "disposable" and the "reusable" tub have equivalent evaporation rates when operated at the same duty ratio.

As also described with reference to FIG. 17, the sample embodiment applies a constant duty ratio of power to the heating element, rather than varying the duty ratio to regulate the temperature of the hot plate. The heating element is a resistive load R, for example 9.6 ohm, to which a constant electrical potential V, for example 24V, that is switched on and off with timing defined by the duty ratio. This is equivalent to driving the heating element with electrical power defined by $P=V^2/R$, for example 60 W at 100% duty ratio.

The duty ratio may be determined in the same manner as the heating element temperature setpoint was determined in the sample embodiments of FIGS. 15 and 16—through characterisation of the device for its performance considering three variables: the ambient absolute humidity, the temperature of gas delivered to the patient and the flow rate at which that gas is delivered.

Two disadvantages of constant duty ratio operation are also overcome by this sample embodiment. The first disadvantage is that the body of water in the humidifier takes much longer to warm tip from a cold start. This is overcome by estimating the temperature threshold in S15 and driving the heating element with 100% duty ratio in S18 until the temperature threshold is reached, then switching to the constant, or fixed, duty level in S21 needed for the desired evaporation rate.

The second disadvantage is that the heating element could reach an excessive temperature once the humidifier tub is empty of water, such as when it has all evaporated. This is overcome by applying a maximum safe temperature of operation in S19, above which the heating element is disabled by setting the duty ratio to 0% in S20.

The sample embodiment of FIG. 17 may also be used to control the humidifier in the absence of the heated tubing. In this case the patient has direct control of the heating element regulated temperature through the user interface (e.g. the knob or dial 10 and/or the control buttons 14) and can adjust it for their comfort, so patients using the reusable tub may tend to set slightly higher temperatures than patients using the disposable tub. Without control of the duty ratio of the power supplied to the heating element, the humidifier would deliver less humidity using the reusable tub than when using the disposable tub, and would offer less comfort benefit of humidification to the patient.

The sample embodiment of FIG. 17 also provides equivalent humidification therapy to all patients, maintaining simplicity.

Humidifier Control Fourth Embodiment

In addition to controlling the duty ratio of the heating element 46 of the humidifier, the controller(s) 40 and/or 44 may also be configured to control the duty ratio of the heating element of the air delivery hose or tube 30. This allows the humidifier to reduce the total capacity of its power supply. The humidifier heating element and the heated tube may share power loading so that while either the humidifier heating element or the heated tube can draw its full current, for example 2.5 A at 24V, instantaneously, they are never active simultaneously. The controller(s) 40 and/or 44 calculate the duty ratio to assign to each of the humidifier and the heated tube so that the combined duty cycle does not exceed 100%. The controller(s) 40 and/or 44 also synchronise the heating cycles in the humidifier and the heated tube so that they do not overlap. The controller(s) 40 and/or 44 may be configured to switch each heating element on and off at timings according to the duty ratios provided by the flow generator so that only one device is on at a time. Such a power management control is disclosed in, for example, U.S. Application 61/095,714, filed Sep. 10, 2008, the entire contents of which are incorporated herein by reference.

According to this sample embodiment, inputs include: 1) temperature setpoint for heated tubing, for example as set by the user interface or a climate control algorithm; 2) temperature sensed by the heated tubing, for example converted from a potential difference across a thermistor; 3) type of heated tubing (15 mm or 19 mm for example); 4) temperature setpoint for humidifier, for example as set by the user interface or a climate control algorithm; and 5) temperature sensed by the humidifier, for example as converted from a potential difference across thermistor.

Outputs of the sample embodiment include: 1) heating power to be applied to humidifier, for example a duty ratio from 0 to 100%; and 2) heating power to be applied to heated tubing, for example a duty ratio from 0 to 100%.

The control also includes the use of constants for the heated tubing, including: 1) a proportional factor Pf; 2) an integral factor If; and 3) a derivative factor Df. Similarly, the control also includes the use of constants for the humidifier, including: 1) a proportional factor Pf; 2) an integral factor If, and 3) a derivative factor Df.

Internal variables include: 1) humidifier temperature sensed on previous reading, Told; 2) humidifier cumulative sum of temperature differences, sumTd; 3) heated tubing temperature sensed on previous reading, Told; and 4) heated tubing cumulative sum of temperature differences, sumTd.

The controller(s) 40 and/or 44 may comprise a simplified proportional-integral control function:

1. Calculate temperature difference Td=this temperature reading minus the previous reading Told.
2. If the measured temperature is close to the setpoint (|Td| is less than 1/Pf),
   a. then multiply Td times integral factor If and add the result to the cumulative sum of temperature differences sumTd,
   b. else reset sumTd to zero.

3. Calculate the duty ratio=Pf*Td+If*sumTd.
4. Trim the duty ratio to be between 0 and 1.

The duty ratios for each of the humidifier and heated tubing are then compared.

1. If the sum of duty for humidifier and heated tubing exceeds 1.0, then one or both duty ratios are reduced. For example, the heated tubing duty ratio is reduced to 0.5 and then the humidifier duty ratio will be reduced as far as necessary.

2. The two duty ratios are multiplied by 100 for output to the humidifier controller as integer values from 0 to 100 (indicating 100%).

Humidifier Control Fifth Embodiment

According to another sample embodiment, the controller(s) 40 and/or 44 may be configured to control the humidifier heating element and the heated tubing using inputs including: 1) air flow rate sensed by flow generator, for example averaged over one minute; 2) ambient relative humidity, for example as determined or sensed by the humidifier; 3) ambient temperature, for example as sensed by the humidifier; 4) a temperature sensed by the heated tubing, for example in ° C., if a heated tube is connected; 5) a heated tubing setting from the user interface, for example in ° C., or an automatic setting; 6) a humidifier setting from the user interface for example an automatic setting, or a 'wetter' or 'dryer' setting than the standard automatic setting; 7) a time stamp.

The outputs of the control may comprise: 1) a temperature setpoint for the humidifier; and 2) a temperature setpoint for the heated tubing.

Constants for the control may comprise: 1) coefficients to convert from relative to absolute humidity, including a) three coefficients to apply to the quadratic function; and 2) a table to determine a temperature setpoint from a desired humidity output of the humidifier.

The table may be a matrix of points from which the setpoint can be trilinearly interpolated, including: a) one axis for average air flow rate, for example corresponding to 10 to 70 L/min at 12 L/min intervals, which provides six points; b) one axis for desired absolute humidity output, for example corresponding to 0 to 40 mg/L at 8 mg/L intervals, which provides six points; and c) one axis for ambient absolute humidity, for example corresponding to 0 to 35 mg/L at 5 mg/L intervals, which provides eight points.

The total matrix size provides 6×6×8=288 data points. Each data point is a temperature from 5 to 95° C. in 0.1° C. increments. The matrix may be, for example, as shown in Table 6 below.

TABLE 6

| Flow | Ambient AH | Desired Added AH | Hot Plate Temp |
|---|---|---|---|
| 10 | 0 | 0 | 5.0 |
| 10 | 0 | 5 | 5.0 |
| 10 | 0 | 10 | 8.3 |
| 10 | 0 | 15 | 25.0 |
| 10 | 0 | 20 | 41.7 |
| 10 | 0 | 25 | 58.3 |
| 10 | 0 | 30 | 75.0 |
| 10 | 0 | 35 | 75.0 |
| 10 | 8 | 0 | 5.0 |
| 10 | 8 | 5 | 5.0 |
| 10 | 8 | 10 | 16.3 |
| 10 | 8 | 15 | 33.0 |
| 10 | 8 | 20 | 49.7 |
| 10 | 8 | 25 | 66.3 |
| 10 | 8 | 30 | 75.0 |
| 10 | 8 | 35 | 75.0 |

TABLE 6-continued

| Flow | Ambient AH | Desired Added AH | Hot Plate Temp |
|---|---|---|---|
| 10 | 16 | 0 | 5.0 |
| 10 | 16 | 5 | 7.7 |
| 10 | 16 | 10 | 24.3 |
| 10 | 16 | 15 | 41.0 |
| 10 | 16 | 20 | 57.7 |
| 10 | 16 | 25 | 74.3 |
| 10 | 16 | 30 | 75.0 |
| 10 | 16 | 35 | 75.0 |
| 10 | 24 | 0 | 5.0 |
| 10 | 24 | 5 | 15.7 |
| 10 | 24 | 10 | 32.3 |
| 10 | 24 | 15 | 49.0 |
| 10 | 24 | 20 | 65.7 |
| 10 | 24 | 25 | 75.0 |
| 10 | 24 | 30 | 75.0 |
| 10 | 24 | 35 | 75.0 |
| 10 | 32 | 0 | 7.0 |
| 10 | 32 | 5 | 23.7 |
| 10 | 32 | 10 | 40.3 |
| 10 | 32 | 15 | 57.0 |
| 10 | 32 | 20 | 73.7 |
| 10 | 32 | 25 | 75.0 |
| 10 | 32 | 30 | 75.0 |
| 10 | 32 | 35 | 75.0 |
| 10 | 40 | 0 | 15.0 |
| 10 | 40 | 5 | 31.7 |
| 10 | 40 | 10 | 48.3 |
| 10 | 40 | 15 | 65.0 |
| 10 | 40 | 20 | 75.0 |
| 10 | 40 | 25 | 75.0 |
| 10 | 40 | 30 | 75.0 |
| 10 | 40 | 35 | 75.0 |
| 22 | 0 | 0 | 5.0 |
| 22 | 0 | 5 | 5.0 |
| 22 | 0 | 10 | 20.3 |
| 22 | 0 | 15 | 37.0 |
| 22 | 0 | 20 | 53.7 |
| 22 | 0 | 25 | 70.3 |
| 22 | 0 | 30 | 75.0 |
| 22 | 0 | 35 | 75.0 |
| 22 | 8 | 0 | 5.0 |
| 22 | 8 | 5 | 11.7 |
| 22 | 8 | 10 | 28.3 |
| 22 | 8 | 15 | 45.0 |
| 22 | 8 | 20 | 61.7 |
| 22 | 8 | 25 | 75.0 |
| 22 | 8 | 30 | 75.0 |
| 22 | 8 | 35 | 75.0 |
| 22 | 16 | 0 | 5.0 |
| 22 | 16 | 5 | 19.7 |
| 22 | 16 | 10 | 36.3 |
| 22 | 16 | 15 | 53.0 |
| 22 | 16 | 20 | 69.7 |
| 22 | 16 | 25 | 75.0 |
| 22 | 16 | 30 | 75.0 |
| 22 | 16 | 35 | 75.0 |
| 22 | 24 | 0 | 11.0 |
| 22 | 24 | 5 | 27.7 |
| 22 | 24 | 10 | 44.3 |
| 22 | 24 | 15 | 61.0 |
| 22 | 24 | 20 | 75.0 |
| 22 | 24 | 25 | 75.0 |
| 22 | 24 | 30 | 75.0 |
| 22 | 24 | 35 | 75.0 |
| 22 | 32 | 0 | 19.0 |
| 22 | 32 | 5 | 35.7 |
| 22 | 32 | 10 | 52.3 |
| 22 | 32 | 15 | 69.0 |
| 22 | 32 | 20 | 75.0 |
| 22 | 32 | 25 | 75.0 |
| 22 | 32 | 30 | 75.0 |
| 22 | 32 | 35 | 75.0 |
| 22 | 40 | 0 | 27.0 |
| 22 | 40 | 5 | 43.7 |
| 22 | 40 | 10 | 60.3 |
| 22 | 40 | 15 | 75.0 |
| 22 | 40 | 20 | 75.0 |

TABLE 6-continued

| Flow | Ambient AH | Desired Added AH | Hot Plate Temp |
|---|---|---|---|
| 22 | 40 | 25 | 75.0 |
| 22 | 40 | 30 | 75.0 |
| 22 | 40 | 35 | 75.0 |
| 34 | 0 | 0 | 5.0 |
| 34 | 0 | 5 | 15.7 |
| 34 | 0 | 10 | 32.3 |
| 34 | 0 | 15 | 49.0 |
| 34 | 0 | 20 | 65.7 |
| 34 | 0 | 25 | 75.0 |
| 34 | 0 | 30 | 75.0 |
| 34 | 0 | 35 | 75.0 |
| 34 | 8 | 0 | 7.0 |
| 34 | 8 | 5 | 23.7 |
| 34 | 8 | 10 | 40.3 |
| 34 | 8 | 15 | 57.0 |
| 34 | 8 | 20 | 73.7 |
| 34 | 8 | 25 | 75.0 |
| 34 | 8 | 30 | 75.0 |
| 34 | 8 | 35 | 75.0 |
| 34 | 16 | 0 | 15.0 |
| 34 | 16 | 5 | 31.7 |
| 34 | 16 | 10 | 48.3 |
| 34 | 16 | 15 | 65.0 |
| 34 | 16 | 20 | 75.0 |
| 34 | 16 | 25 | 75.0 |
| 34 | 16 | 30 | 75.0 |
| 34 | 16 | 35 | 75.0 |
| 34 | 24 | 0 | 23.0 |
| 34 | 24 | 5 | 39.7 |
| 34 | 24 | 10 | 56.3 |
| 34 | 24 | 15 | 73.0 |
| 34 | 24 | 20 | 75.0 |
| 34 | 24 | 25 | 75.0 |
| 34 | 24 | 30 | 75.0 |
| 34 | 24 | 35 | 75.0 |
| 34 | 32 | 0 | 31.0 |
| 34 | 32 | 5 | 47.7 |
| 34 | 32 | 10 | 64.3 |
| 34 | 32 | 15 | 75.0 |
| 34 | 32 | 20 | 75.0 |
| 34 | 32 | 25 | 75.0 |
| 34 | 32 | 30 | 75.0 |
| 34 | 32 | 35 | 75.0 |
| 34 | 40 | 0 | 39.0 |
| 34 | 40 | 5 | 55.7 |
| 34 | 40 | 10 | 72.3 |
| 34 | 40 | 15 | 75.0 |
| 34 | 40 | 20 | 75.0 |
| 34 | 40 | 25 | 75.0 |
| 34 | 40 | 30 | 75.0 |
| 34 | 40 | 35 | 75.0 |
| 46 | 0 | 0 | 11.0 |
| 46 | 0 | 5 | 27.7 |
| 46 | 0 | 10 | 44.3 |
| 46 | 0 | 15 | 61.0 |
| 46 | 0 | 20 | 75.0 |
| 46 | 0 | 25 | 75.0 |
| 46 | 0 | 30 | 75.0 |
| 46 | 0 | 35 | 75.0 |
| 46 | 8 | 0 | 19.0 |
| 46 | 8 | 5 | 35.7 |
| 46 | 8 | 10 | 52.3 |
| 46 | 8 | 15 | 69.0 |
| 46 | 8 | 20 | 75.0 |
| 46 | 8 | 25 | 75.0 |
| 46 | 8 | 30 | 75.0 |
| 46 | 8 | 35 | 75.0 |
| 46 | 16 | 0 | 27.0 |
| 46 | 16 | 5 | 43.7 |
| 46 | 16 | 10 | 60.3 |
| 46 | 16 | 15 | 75.0 |
| 46 | 16 | 20 | 75.0 |
| 46 | 16 | 25 | 75.0 |
| 46 | 16 | 30 | 75.0 |
| 46 | 16 | 35 | 75.0 |
| 46 | 24 | 0 | 35.0 |
| 46 | 24 | 5 | 51.7 |
| 46 | 24 | 10 | 68.3 |
| 46 | 24 | 15 | 75.0 |
| 46 | 24 | 20 | 75.0 |
| 46 | 24 | 25 | 75.0 |
| 46 | 24 | 30 | 75.0 |
| 46 | 24 | 35 | 75.0 |
| 46 | 32 | 0 | 43.0 |
| 46 | 32 | 5 | 59.7 |
| 46 | 32 | 10 | 75.0 |
| 46 | 32 | 15 | 75.0 |
| 46 | 32 | 20 | 75.0 |
| 46 | 32 | 25 | 75.0 |
| 46 | 32 | 30 | 75.0 |
| 46 | 32 | 35 | 75.0 |
| 46 | 40 | 0 | 51.0 |
| 46 | 40 | 5 | 67.7 |
| 46 | 40 | 10 | 75.0 |
| 46 | 40 | 15 | 75.0 |
| 46 | 40 | 20 | 75.0 |
| 46 | 40 | 25 | 75.0 |
| 46 | 40 | 30 | 75.0 |
| 46 | 40 | 35 | 75.0 |
| 58 | 0 | 0 | 23.0 |
| 58 | 0 | 5 | 39.7 |
| 58 | 0 | 10 | 56.3 |
| 58 | 0 | 15 | 73.0 |
| 58 | 0 | 20 | 75.0 |
| 58 | 0 | 25 | 75.0 |
| 58 | 0 | 30 | 75.0 |
| 58 | 0 | 35 | 75.0 |
| 58 | 8 | 0 | 31.0 |
| 58 | 8 | 5 | 47.7 |
| 58 | 8 | 10 | 64.3 |
| 58 | 8 | 15 | 75.0 |
| 58 | 8 | 20 | 75.0 |
| 58 | 8 | 25 | 75.0 |
| 58 | 8 | 30 | 75.0 |
| 58 | 8 | 35 | 75.0 |
| 58 | 16 | 0 | 39.0 |
| 58 | 16 | 5 | 55.7 |
| 58 | 16 | 10 | 72.3 |
| 58 | 16 | 15 | 75.0 |
| 58 | 16 | 20 | 75.0 |
| 58 | 16 | 25 | 75.0 |
| 58 | 16 | 30 | 75.0 |
| 58 | 16 | 35 | 75.0 |
| 58 | 24 | 0 | 47.0 |
| 58 | 24 | 5 | 63.7 |
| 58 | 24 | 10 | 75.0 |
| 58 | 24 | 15 | 75.0 |
| 58 | 24 | 20 | 75.0 |
| 58 | 24 | 25 | 75.0 |
| 58 | 24 | 30 | 75.0 |
| 58 | 24 | 35 | 75.0 |
| 58 | 32 | 0 | 55.0 |
| 58 | 32 | 5 | 71.7 |
| 58 | 32 | 10 | 75.0 |
| 58 | 32 | 15 | 75.0 |
| 58 | 32 | 20 | 75.0 |
| 58 | 32 | 25 | 75.0 |
| 58 | 32 | 30 | 75.0 |
| 58 | 32 | 35 | 75.0 |
| 58 | 40 | 0 | 63.0 |
| 58 | 40 | 5 | 75.0 |
| 58 | 40 | 10 | 75.0 |
| 58 | 40 | 15 | 75.0 |
| 58 | 40 | 20 | 75.0 |
| 58 | 40 | 25 | 75.0 |
| 58 | 40 | 30 | 75.0 |
| 58 | 40 | 35 | 75.0 |
| 70 | 0 | 0 | 35.0 |
| 70 | 0 | 5 | 51.7 |
| 70 | 0 | 10 | 68.3 |
| 70 | 0 | 15 | 75.0 |
| 70 | 0 | 20 | 75.0 |
| 70 | 0 | 25 | 75.0 |
| 70 | 0 | 30 | 75.0 |

TABLE 6-continued

| Flow | Ambient AH | Desired Added AH | Hot Plate Temp |
|---|---|---|---|
| 70 | 0 | 35 | 75.0 |
| 70 | 8 | 0 | 43.0 |
| 70 | 8 | 5 | 59.7 |
| 70 | 8 | 10 | 75.0 |
| 70 | 8 | 15 | 75.0 |
| 70 | 8 | 20 | 75.0 |
| 70 | 8 | 25 | 75.0 |
| 70 | 8 | 30 | 75.0 |
| 70 | 8 | 35 | 75.0 |
| 70 | 16 | 0 | 51.0 |
| 70 | 16 | 5 | 67.7 |
| 70 | 16 | 10 | 75.0 |
| 70 | 16 | 15 | 75.0 |
| 70 | 16 | 20 | 75.0 |
| 70 | 16 | 25 | 75.0 |
| 70 | 16 | 30 | 75.0 |
| 70 | 16 | 35 | 75.0 |
| 70 | 24 | 0 | 59.0 |
| 70 | 24 | 5 | 75.0 |
| 70 | 24 | 10 | 75.0 |
| 70 | 24 | 15 | 75.0 |
| 70 | 24 | 20 | 75.0 |
| 70 | 24 | 25 | 75.0 |
| 70 | 24 | 30 | 75.0 |
| 70 | 24 | 35 | 75.0 |
| 70 | 32 | 0 | 67.0 |
| 70 | 32 | 5 | 75.0 |
| 70 | 32 | 10 | 75.0 |
| 70 | 32 | 15 | 75.0 |
| 70 | 32 | 20 | 75.0 |
| 70 | 32 | 25 | 75.0 |
| 70 | 32 | 30 | 75.0 |
| 70 | 32 | 35 | 75.0 |
| 70 | 40 | 0 | 75.0 |
| 70 | 40 | 5 | 75.0 |
| 70 | 40 | 10 | 75.0 |
| 70 | 40 | 15 | 75.0 |
| 70 | 40 | 20 | 75.0 |
| 70 | 40 | 25 | 75.0 |
| 70 | 40 | 30 | 75.0 |
| 70 | 40 | 35 | 75.0 |

Internal variables may comprise: 1) absolute humidity of ambient; 2) absolute humidity to target at mask; 3) absolute humidity to be added by humidifier; and 4) previous flow rates measured.

In order to generate the temperature setpoint for the humidifier, the controller(s) 40 and/or 44:

1. Calculate ambient absolute humidity from ambient relative humidity and temperature according to: absolute humidity=relative humidity (as a proportion of 1)×(a+b× temp+c×temp×temp) given constant coefficients a=7.264, b=0.0928 and c=0.0293.

2. Calculate target absolute humidity from temperature sensed by heated tubing. If the heated tubing is not available, the ambient temperature may be applied instead. The function is the same quadratic as used in step 1, but the relative humidity is now set by the user interface.

3. Calculate absolute humidity to be added by humidifier by subtracting the ambient absolute humidity from the target.

4. Calculate the temperature setpoint for humidifier from the absolute humidity to be added, the flow rate and the ambient temperature. The calculation is a trilinear interpolation of Table 6.

In order to generate the temperature setpoint for the heated tubing:

1. A default temperature setpoint corresponds to the setting on the user interface.

2. If there has been a sudden fall in flow rate, the temperature setpoint is adjusted slightly (e.g. a few ° C.) above the setpoint for a limited duration (e.g. 15 min).

Flow Generator Design Considerations

When the humidifier is fitted to or removed from the flow generator, the flow generator user interface may indicate detection or removal of the humidifier within, for example, one second. When a heated tubing is fitted to or disconnected from the humidifier, the flow generator user interface may indicate detection or removal of the heated tubing within, for example, one second.

As discussed above, the flow generator controller may control the humidifier and the heated tubing. The flow generator controller may use constants stored in the humidifier controller and comprising, for example, six control parameters, each a value between 0 and 1 with 0.01 resolution and a matrix of 6×6×8=288 data points. Each data point may be a temperature from 5 to 95° C. with 0.1° C. resolution.

During therapy the flow generator may poll the humidifier for the readings of humidifier heating element and the heated tubing temperature, for example, at least once every 10 seconds. During therapy the flow generator may poll the humidifier for the readings of ambient temperature and relative humidity, for example, at least once every 60 seconds.

Temperatures may be communicated as values from 5 to 95° C. with 0.1° C. resolution. Relative humidity may be communicated as an integer value from 0 to 100. Values outside this range shall be limited to this range.

The flow generator may calculate the duty ratio to be applied by the humidifier as an integer value between 0 and 100 (where 100 indicates 100% duty). The flow generator may also calculate the duty ratio to be applied to the heated tubing as an integer value between 0 and 100 (where 100 indicates 100% duty). The flow generator may ensure that the sum of the duty ratios for the humidifier and heated tubing does not exceed 100 (indicates 100%).

During therapy, requests from the flow generator to set the humidifier duty ratio may be transmitted, for example, at least once every 3 seconds and requests from the flow generator to set the heated tubing duty ratio may be transmitted, for example, at least once every 1 second.

Humidifier Design Considerations

When both the heated tubing and the humidifier are commanded to heat, the controller(s) 40 and/or 44 may ensure that the power is distributed such that both items are not drawing power at the same instant. To achieve this, the heated tubing and the humidifier may be controlled by the same controller.

A suitable communications protocol may be developed to enable the flow generator to communicate with the humidifier and the power supply and any other devices that may be added. The communications protocol may utilize, for example, a 16-bit CRC to detect communications errors. The communications between the flow generator and the humidifier may be half-duplex to minimize the number of pins in the wiring connectors.

The humidifier may transmit the following information to the FG on demand: 1) humidifier status (ok or error); 2) relative humidity reading; 3) temperature at which the relative humidity reading was made; 4) temperature of the heating element in the humidifier; 5) humidifier heating duty ratio.

The humidifier may respond to the following commands from the flow generator: 1) request for humidifier status; 2) request for humidity reading; 3) request for temperature of humidity reading; 4) request for temperature of the heating element in the humidifier; 5) set the heating duty ratio in the humidifier.

The humidifier may cease heating the humidifier tub unless a request setting the heating duty ratio is received at least every 10 seconds.

Heated Tube Design Considerations

The humidifier may transmit the following information to the flow generator on demand: 1) heater tube status, including a) the presence or absence of a heated tubing, b) the diameter of the heater tube (15 mm or 19 mm for example), and c) ok or error; 2) temperature in the heater tube; and 3) humidifier heating duty ratio.

The humidifier may respond to the following commands from the flow generator: 1) request for heater tube status; 2) request for temperature in the heater tube; 3) set the heating power level in the humidifier.

The humidifier may cease heating the heater tube unless a request setting the heating duty ratio is received, for example, at least every 1 second.

Temperature Conversions

The controller(s) 40 and/or 44 may convert the potential measured across a thermistor into a temperature, for example in ° C., using a lookup table. Three tables are required: 1) and 2) a temperature conversion table for each type of heated tubing (e.g. 15 mm and 19 mm) (at 0.1° C. resolution for range 5 to 40° C., having approximately 360 data points in each of two tables); and 3) a temperature conversion table for the humidifier (at 0.1° C. resolution for range 5 to 95° C., having approximately 960 data points). Each may be a lookup table indexed by being evenly spaced on the axis of thermistor potential.

Upload of Climate Control Constants to Flow Generator

The humidifier may carry a table, for example Table 6, as a constant and transfer it to the flow generator before climate control begins. This is so that humidifier upgrades may be implemented in the humidifier without the need to upgrade the flow generator software.

Indicator Lights

On command from the flow generator, for example using commands over a serial communications link, the humidifier may directly control one blue and one amber LED. The humidifier may control the indicator lights according to commands received from the flow generator and each command may include the following information: 1) colour—blue or amber; 2) brightness—bright, dim or off, and 3) Fading—yes or no.

If fading is: 1) yes, the brightness shall transition smoothly over three seconds; or 2) no, the brightness shall switch to the new level. The humidifier may be able to fade changes on both indicators simultaneously, e.g. for a cross-fade the flow generator may send two commands together—one command to fade one indicator off and a second command to fade the other indicator on.

Humidifier Control Sixth Embodiment

Patients sleeping with a humidifier set to deliver humidity below saturation in the tubing may suffer from condensation in the tubing in three circumstances: 1) a drop in ambient temperature, so the air cools in the tubing to below its dew point; 2) a rise in ambient humidity, so the air leaving the humidifier rises in humidity and then cools in the tubing to below its dew point; and 3) a drop in flow rate, such as when autosetting lowers the treatment pressure, so the humidifier adds more humidity to the air, and then the air cools in the tubing to below its dew point.

The advice currently given to patients to deal with the problem of condensation, or rain out, in the tube includes running the tubing under the bedclothes to reduce cooling in the tubing and/or setting the humidifier to a lower heat setting. These approaches result in the patient receiving less humidity all night to provide more margin from the dew point, to allow for changes during the night.

As discussed above, sample embodiments provide implementation of climate control to deliver a predetermined temperature and humidity of air to the mask end of the tubing. However, climate control as described with reference to the previous sample embodiments requires a temperature sensor in the tubing to monitor the temperature of the air in the tubing. There is increased cost in the heated tubing with temperature sensing, so it would be an advantage to offer a patient some relief from condensation in a system with conventional, i.e. unheated, tubing.

Figure 18:
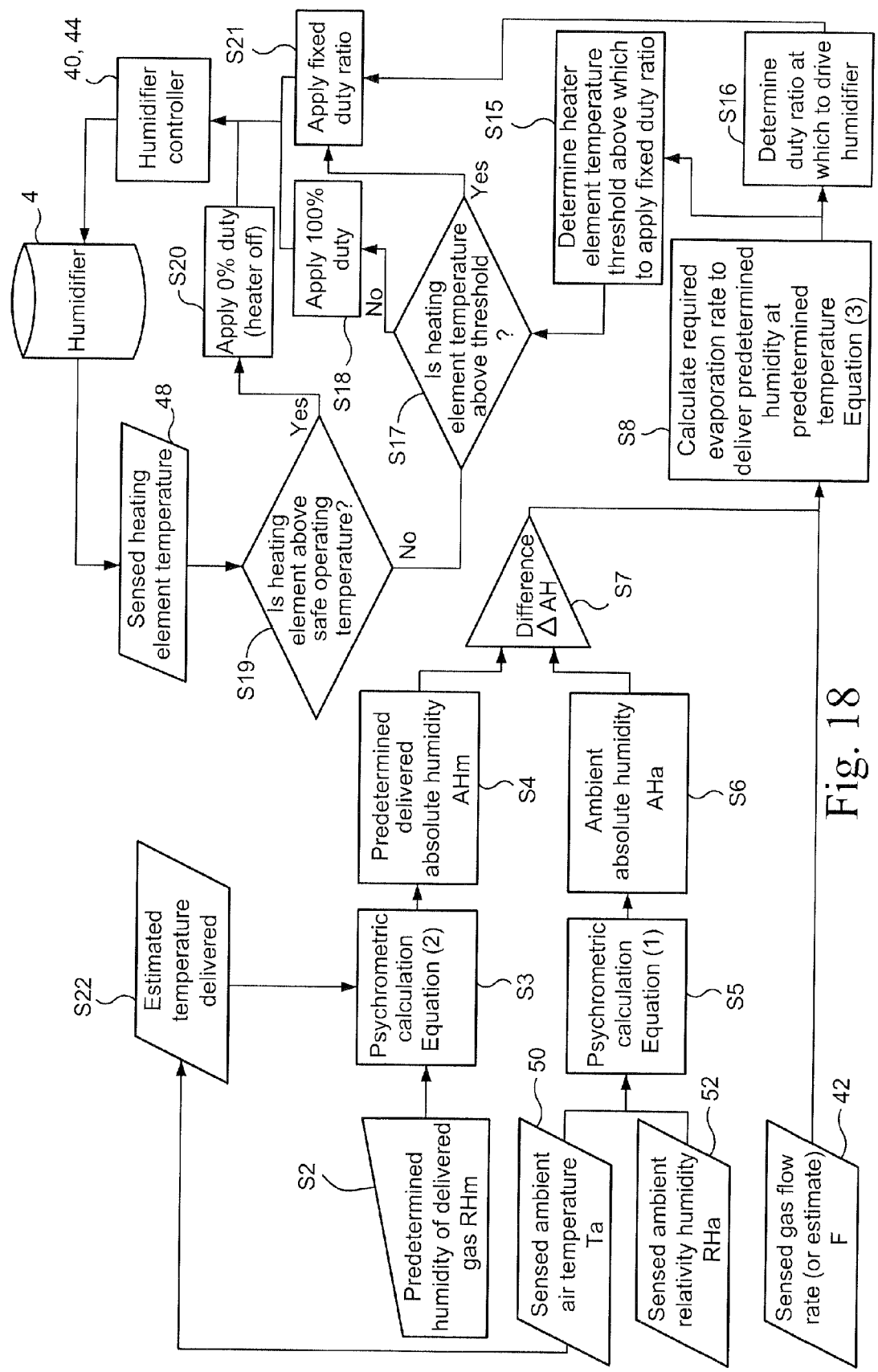
FIG. 18 schematically depicts a control of the respiratory apparatus according to another sample embodiment.

Referring to FIG. 18, according to another sample embodiment, climate control is provided in which the tubing is not heated and the delivered air temperature is not measured, but rather is estimated in S22 from the readings of the ambient temperature sensor. The estimate is based on characterisation of the temperature differences between the ambient temperature reported and the delivered air temperature under different conditions of ambient temperature and air flow and sources of heat in the device such as a power supply, a motor, electronics, or the humidifier heating element.

As discussed above, Comparative Example 1 (Table 2) shows the response that the sample embodiments discussed above with respect to FIGS. 15 and 16 would have to a change in ambient temperature with no change in ambient absolute humidity and no control of the mask temperature Tm. According to this sample embodiment in which the delivered air temperature Tm is not measured, but rather estimated, an equivalent table for the adjustment in water temperature to a change in ambient humidity is shown below in Table 7 for three different options of ambient air temperature.

TABLE 7

| Water temperature deg C. | Ambient air temperature deg C. | Ambient air absolute humidity (mg/L) | Air relative humidity | Humidification output mg/L | Temp of air delivered deg C. | Humidity of air delivered (mg/L) | Humidity of air delivered % RH |
|---|---|---|---|---|---|---|---|
| 48.6 | 15 | 4  | 32% | 8.5 | 15 | 12.5 | 100% |
| 46   | 15 | 6  | 48% | 6.5 | 15 | 12.5 | 100% |
| 42.5 | 15 | 8  | 64% | 4.4 | 15 | 12.4 | 100% |
| 38.3 | 15 | 10 | 80% | 2.4 | 15 | 12.4 | 100% |
| 31   | 15 | 12 | 96% | 0.4 | 15 | 12.4 | 100% |
| 50.5 | 20 | 8  | 47% | 9.1 | 20 | 17.1 | 100% |
| 47.8 | 20 | 10 | 58% | 7.2 | 20 | 17.2 | 100% |
| 44.5 | 20 | 12 | 70% | 5.2 | 20 | 17.2 | 100% |
| 40   | 20 | 14 | 82% | 3.1 | 20 | 17.1 | 100% |

TABLE 7-continued

| Water temperature deg C. | Ambient air temperature deg C. | Ambient air absolute humidity (mg/L) | Air relative humidity | Humidification output mg/L | Temp of air delivered deg C. | Humidity of air delivered (mg/L) | Humidity of air delivered % RH |
|---|---|---|---|---|---|---|---|
| 34 | 20 | 16 | 93% | 1.2 | 20 | 17.2 | 100% |
| 51.8 | 25 | 14 | 60% | 9.3 | 25 | 23.3 | 100% |
| 49 | 25 | 16 | 69% | 7.3 | 25 | 23.3 | 100% |
| 45.5 | 25 | 18 | 77% | 5.2 | 25 | 23.2 | 100% |
| 41.5 | 25 | 20 | 86% | 3.3 | 25 | 23.3 | 100% |
| 35 | 25 | 22 | 95% | 1.2 | 25 | 23.2 | 100% |

A feature of this sample embodiment is that the delivered air temperature is estimated such that the device does not detect whether the tubing is insulated from ambient temperature, such as with a cloth cover or bedding. Insulation can increase the delivered air temperature by reducing cooling in the tubing. To minimise the chance of condensation the tubing may be assumed to have no insulation and therefore the delivered air is cooler and closer to its dew point than if insulation is fitted.

It should be appreciated that the system of this sample embodiment will respond appropriately to simultaneous changes in ambient temperature and ambient humidity and air flow rate. The system of this sample embodiment provides protection against condensation in the tubing throughout the night, regardless of changes in ambient temperature, humidity and flow. The system of this sample embodiment also offers completely automatic control of the humidifier. Assuming a default value for the predetermined relative humidity of the delivered gas, the patient need never adjust the humidifier. The system of this sample embodiment also offers a setting of humidity through the user interface, which can be translated into a predetermined relative humidity of the delivered gas.

Unlike the other sample embodiments which include heated tubing, this sample embodiment cannot deliver warmer air, or the higher humidity that can be carried by warmer air. This sample embodiment also does not allow the patient to select the temperature of air delivered. This sample embodiment also does not raise the humidity delivered if the tubing is insulated. Changing the setting for humidity through the user interface could overcome this.

The humidifier control according to this sample embodiment allows the respiratory apparatus to be provided with standard tubing rather than heated tubing, thus reducing the cost of the system.

The sample embodiments discussed above may also be implemented entirely in software or hardware (e.g. an ASIC), so the humidifier may be configured to operate as any of the three sample embodiments with no increase in the device cost of goods.

The humidifier according to the sample embodiments disclosed herein improve user compliance due to increased comfort, reduced likelihood of dry/sore throat, and/or improved ease of use from the provision of an automatic optimum humidification setting.

The humidifier according to the sample embodiments disclosed herein also provides a solution to a problem found in prior art humidifiers that only track room ambient temperature and flow, which is that such humidifiers may be tracking an inappropriate humidification output due to human error/confusion in making the original setting. A user of such humidifiers does not know which setting is closest to the optimum humidification level for any given condition, particularly whenever they experience a significant change to their usual environment/climate, e.g. during travel.

The humidifiers and respiratory apparatus according to the sample embodiments disclosed herein measure ambient relative humidity and pressure (altitude compensation), as well as ambient temperature, to improve accuracy in the delivered humidification level compared to prior art systems that do not sense ambient humidity and pressure. The availability of low cost humidity and pressure sensors in recent years now makes monitoring of these additional parameters feasible and practical even in CPAP devices.

The humidifier and respiratory apparatus according to the sample embodiments disclosed herein will respond to detection of sustained mouth leak, but unlike prior art systems, will correct the humidification output to the optimum moisture density, rather than just to an arbitrary setting which is likely not close to optimum.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the invention relates.

What is claimed is:

1. A humidifier for a respiratory apparatus for delivering a humidified flow of breathable gas to a patient, the humidifier comprising:
   a humidifier chamber configured to store a supply of water to humidify the flow of breathable gas, the humidifier chamber comprising a first heating element configured to heat the supply of water;
   a humidity sensor to detect an ambient humidity of the patient's environment and generate signals indicative of the ambient humidity; and
   a controller configured to receive the signals from the humidity sensor and control the first heating element to provide a predetermined humidity to the flow of breathable gas based on a difference between an ambient absolute humidity corresponding to the detected ambient humidity and a predetermined absolute humidity that corresponds to the predetermined humidity,
   wherein the controller is configured to calculate an evaporation rate of the supply of water required to provide the difference between the ambient absolute humidity and the predetermined absolute humidity,
   wherein the evaporation rate is determined by multiplying a flow rate of the flow of breathable gas and the difference between the predetermined absolute humidity and the ambient absolute humidity, and
   wherein the flow rate corresponds to a vent flow from a patient interface at a pressure of the flow of breathable gas.

2. A humidifier according to claim 1, wherein the controller is further configured to control the first heating element to provide the flow of humidified breathable gas at a predetermined temperature.

3. A humidifier according to claim 2, wherein the predetermined humidity is a predetermined relative humidity and the controller is configured to determine the predetermined absolute humidity based on the predetermined relative humidity and the predetermined temperature.

4. A humidifier according to claim 3, further comprising a user input configured to permit the patient or a clinician to select the predetermined temperature and/or the predetermined relative humidity.

5. A humidifier according to claim 4, wherein the user input comprises a control knob.

6. A humidifier according to claim 3, wherein the controller is configured to calculate the ambient absolute humidity according to the formula $AHa = RHa \cdot (K_1 - K_2 \cdot Ta + K_3 \cdot Ta^2)$, wherein AHa is ambient absolute humidity, RHa is an ambient relative humidity and Ta is an ambient temperature, and is configured to calculate the predetermined absolute humidity according to the formula $AHp = RHp \cdot (K_1 - K_2 \cdot Tp + K_3 \cdot Tp^2)$, wherein AHp is the predetermined absolute humidity, RHp is the predetermined relative humidity, Tp is the predetermined temperature, and $K_1$, $K_2$, and $K_3$ are coefficients.

7. A humidifier according to claim 3, further comprising a flow rate sensor configured to determine the flow rate and generate signals indicative of the flow rate.

8. A humidifier according to claim 2, wherein the predetermined temperature is about 15° C.-37° C.

9. A humidifier according to claim 2, wherein the predetermined temperature is about 26°-28° C.

10. A humidifier according to claim 2 further comprising a user input configured to permit the patient or a clinician to select the predetermined temperature and/or the predetermined absolute humidity.

11. A humidifier according to claim 1, wherein the predetermined absolute humidity is about 11- 44 mg/L.

12. A humidifier according to claim 1, wherein the predetermined humidity is a predetermined relative humidity of about 50%-100%.

13. A humidifier according to claim 1, wherein the predetermined humidity is a predetermined relative humidity of about 70%-90%.

14. A humidifier according to claim 1, further comprising a temperature sensor to detect a temperature of the supply of water or a temperature of the first heating element and generate signals indicative of the temperature of the supply of water or the temperature of the first heating element, respectively, wherein the controller is configured to control the first heating element in a feedback loop of the signals generated by the temperature sensor.

15. A humidifier according to claim 1, wherein the controller is configured to control the first heating element to increase the temperature of the supply of water as a flow rate of the flow of breathable gas increases and decrease temperature of the supply of water as the flow rate decreases.

16. A humidifier according to claim 1, wherein the controller is configured to control the first heating element to decrease the temperature of the supply of water as the ambient absolute humidity increases, and to increase the temperature of the supply of water as the ambient absolute humidity decreases.

17. A humidifier according to claim 1, wherein the controller is configured to control the first heating element to increase the temperature of the supply of water as a predetermined temperature of the flow of breathable gas increases, and to decrease the temperature of the supply of water as the predetermined temperature of the flow of breathable gas decreases.

18. A humidifier according to claim 1, wherein a plurality of predetermined temperatures, a plurality of predetermined relative humidities, and a plurality of corresponding predetermined absolute humidities are stored in memory operatively associated with the controller.

19. A humidifier according to claim 1, further comprising a delivery hose configured to deliver the humidifier flow of breathable gas to the patient, the delivery hose comprising a first end configured for connection to an outlet of the humidifier, a second end configured for connection to a patient interface, and a second heating element configured to heat the humidified flow of breathable gas in the delivery hose.

20. A humidifier according to claim 19, further comprising a temperature sensor at the second end of the delivery hose configured to detect a temperature of the humidified flow of the breathable gas at the second end of the delivery hose and generate signals indicative of the detected temperature of the humidified flow of the breathable gas at the second end of the delivery hose.

21. A humidifier according to claim 20, wherein the controller is configured to control the second heating element in response to the signals from the temperature sensor to provide the humidified flow of breathable gas at the second end of the delivery hose at a predetermined temperature and a predetermined relative humidity.

22. A humidifier according to claim 20, wherein the controller is configured to determine a change in a rate of the humidified flow of breathable gas and control the second heating element to adjust a predetermined temperature of the humidified flow of breathable gas when the change in the flow rate exceeds a predetermined flow rate change.

23. A humidifier according to claim 22, wherein the controller is configured to control the second heating element to increase the predetermined temperature of the humidified flow of breathable gas when the change in the flow rate exceeds a predetermined decrease in the flow rate.

24. A humidifier according to claim 23, wherein the controller is configured to control the second heating element to increase the predetermined temperature of the humidified flow of the breathable gas above a saturation temperature.

25. A humidifier according to claim 24, wherein the controller is configured to control the first heating element to decrease the temperature of the supply of water when the change in the flow rate exceeds the predetermined decrease in the flow rate.

26. A humidifier according to claim 25, wherein the controller is configured to control the second heating element to decrease the predetermined temperature of the humidified flow of the breathable gas at a predetermined time after the first heating element is controlled to decrease the temperature of the supply of water.

27. A humidifier according to claim 22, wherein the controller is configured to control the second heating element to decrease the predetermined temperature of the humidified flow of the breathable gas when the change in the flow rate exceeds a predetermined increase in the flow rate.

28. A humidifier according to claim 19, wherein the predetermined absolute humidity corresponds to a predetermined temperature and a predetermined relative humidity at the second end of the delivery hose.

29. A humidifier according to claim 28, wherein the predetermined temperature at the second end of the delivery hose is equal to or greater than an ambient temperature.

30. A humidifier according to claim 19, wherein the controller is configured to control a duty ratio of each of the first heating element and the second heating element.

31. A humidifier according to claim 1, wherein the controller is configured to control a duty ratio of the first heating element.

32. A respiratory apparatus for providing a humidified flow of breathable gas to a patient, comprising:
a flow generator to generate a flow of breathable gas; and
a humidifier according to claim 1.

33. A humidifier according to claim 1, wherein the predetermined humidity corresponds to a target humidity level selected from a plurality of target humidity settings, and each target humidity setting corresponds to a heater setting that sets a target temperature for the first heating element or sets a target temperature for the supply of water, and
wherein the controller is configured to continuously calibrate each of the plurality of target humidity settings to different heater settings based on at least one ambient condition.

34. A humidifier according to claim 33, wherein the at least one ambient condition comprises one or more of temperature, absolute humidity and relative humidity.

35. A humidifier according to claim 1, wherein the controller is configured to adjust the flow rate of the flow of breathable gas in response to a leak at the patient interface.

36. A method of humidifying a flow of breathable gas to be provided to a patient, the method comprising:
determining an ambient humidity of the ambient air of the patient's environment; and
controlling the humidifier of claim 1 to adjust a temperature of the supply of water and provide the predetermined humidity to the flow of breathable gas.

37. A method according to claim 36, wherein the predetermined humidity is an absolute humidity of about 11-44 mg/L.

38. A method according to claim 36, wherein the predetermined humidity is an absolute humidity of about 14 mg/L.

39. A method according to claim 36, wherein the predetermined humidity is a relative humidity of about 50%-100%.

40. A method according to claim 36, further comprising selecting the predetermined humidity.

41. A method according to claim 36, further comprising:
detecting the temperature of the supply of water or a temperature of the first heating element configured to heat the supply of water;
generating signals indicative of the temperature of the supply of water or the temperature of the first heating element, respectively; and
controlling the heating element in a feedback loop of the signals to control the temperature of the supply of water.

42. A method according to claim 41, further comprising: controlling a duty ratio of the first heating element.

43. A method according to claim 36, further comprising determining the ambient absolute humidity according to the formula $AHa = RHa \cdot (K_1 - K_2 \cdot Ta + K_3 \cdot Ta^2)$, wherein AHa is the ambient absolute humidity, RHa is an ambient relative humidity, Ta is an ambient temperature, and $K_1$, $K_2$, and $K_3$ are coefficients.

44. A method according to claim 43, wherein controlling the temperature of the supply of water comprises decreasing the temperature of the supply of water as the ambient absolute humidity increases, and increasing the temperature of the supply of water as the ambient absolute humidity decreases.

45. A method according to claim 36, wherein the predetermined humidity is an absolute humidity determined according to the formula $AHp = RHp \cdot (K_1 - K_2 \cdot Tp + K_3 \cdot Tp^2)$, wherein AHp is predetermined humidity, RHp is a predetermined relative humidity, and Tp is a predetermined temperature.

46. A method according to claim 36, wherein controlling the temperature of the supply of water comprises determining an evaporation rate of the supply of water.

47. A method according to claim 46, wherein the evaporation rate is determined by multiplying a flow rate of the flow of breathable gas and the difference between the predetermined absolute humidity and the ambient absolute humidity.

48. A method according to claim 47, further comprising detecting the flow rate of the flow of breathable gas.

49. A method according to claim 47, wherein the flow rate corresponds to a vent flow from a patient interface, connected to a delivery hose, at a pressure of the flow of breathable gas.

50. A method according to claim 47, wherein controlling the temperature of the supply of water comprises increasing the temperature of the supply of water as the flow rate increases and decreasing the temperature of the supply of water as the flow rate decreases.

51. A method according to claim 36, wherein controlling the temperature of the supply of water comprises increasing the temperature of the supply of water as a predetermined temperature of the humidified flow of the breathable gas increases, and decreasing the temperature of the supply of water as the predetermined temperature of the humidified flow of the breathable gas decreases.

52. A method according to claim 36, further comprising:
  detecting a temperature of the humidified flow of the breathable gas at an end of a delivery hose configured to be connected to a patient interface;
  generating signals indicative of the temperature of the humidified flow at the end of the delivery hose; and
  controlling a delivery hose heating element in response to the signals to provide the humidified flow at the end of the delivery hose at a predetermined temperature of the humidified flow of the breathable gas.

53. A method according to claim 52, wherein the predetermined temperature at the end of the delivery hose is equal to or greater than the ambient air temperature.

54. A method according to claim 52, further comprising:
  determining a change in the rate of the humidified flow of breathable gas; and
  controlling the delivery hose heating element to adjust the predetermined temperature when the change in the flow rate exceeds a predetermined flow rate change.

55. A method according to claim 54, wherein the delivery hose heating element is controlled to increase the predetermined temperature when the change in the flow rate exceeds a predetermined decrease in the flow rate.

56. A method according to claim 55, wherein the delivery hose heating element is controlled to increase the predetermined temperature above a saturation temperature.

57. A method according to claim 56, further comprising:
  decreasing the temperature of the supply of water when the change in the flow rate exceeds the predetermined decrease in the flow rate.

58. A method according to claim 57, further comprising:
  controlling the delivery hose heating element to decrease the predetermined temperature at a predetermined time after decreasing the temperature of the supply of water.

59. A method according to claim 54, further comprising:
  controlling the delivery hose heating element to decrease the predetermined temperature when the change in the flow rate exceeds a predetermined increase in the flow rate.

60. A method according to claim 52, further comprising:
  controlling a duty ratio of the delivery hose heating element.

61. A humidifier for a respiratory apparatus for delivering a humidified flow of breathable gas to a patient, the humidifier comprising:
  a humidifier chamber configured to store a supply of water to humidify the flow of breathable gas, the humidifier chamber comprising a first heating element configured to heat the supply of water;
  a delivery hose comprising a first end configured for connection to an outlet of the humidifier chamber, a second end configured for connection to a patient interface, and a second heating element configured to heat the humidified flow of breathable gas in the delivery hose;
  a relative humidity sensor to detect a relative humidity of ambient air of the patient's environment and generate signals indicative of the ambient relative humidity;
  a first temperature sensor to detect a temperature of the ambient air and generate signals indicative of the ambient temperature;
  a second temperature sensor at the second end of the delivery hose configured to detect a temperature of the humidified flow at the second end of the delivery hose and generate signals indicative of the detected temperature of the humidified flow; and
  a controller configured to determine an absolute humidity of the ambient air from the signals generated by the relative humidity sensor and the first temperature sensor and to control the first heating element to provide a predetermined relative humidity to the flow of breathable gas based on a comparison between the determined absolute humidity of the ambient air and a condition of the breathable gas within the respiratory apparatus,
  wherein the controller is configured to control the second heating element in response to the signals from the second temperature sensor to provide the humidified flow at the second end of the delivery hose at a predetermined temperature and the predetermined relative humidity,
  wherein the controller is configured to determine a change in the rate of the flow of breathable gas and control the second heating element to adjust the predetermined temperature when the change in the flow rate exceeds a predetermined flow rate change, and
  wherein the controller is configured to control the second heating element to decrease the predetermined temperature when the change in the flow rate exceeds a predetermined increase in the flow rate.

62. A humidifier for a respiratory apparatus for delivering a humidified flow of breathable gas to a patient, the humidifier comprising:
  a humidifier chamber configured to store a supply of water to humidify the flow of breathable gas, the humidifier chamber comprising a first heating element configured to heat the supply of water;
  a delivery hose comprising a first end configured for connection to an outlet of the humidifier chamber, a second end configured for connection to a patient interface, and a second heating element configured to heat the humidified flow of the breathable gas in the delivery hose;
  a relative humidity sensor to detect a relative humidity of ambient air of the patient's environment and generate signals indicative of the ambient relative humidity;
  a first temperature sensor to detect a temperature of the ambient air and generate signals indicative of the ambient temperature;
  a second temperature sensor at the second end of the delivery hose configured to detect a temperature of the humidified flow at the second end of the delivery hose and generate signals indicative of the detected temperature of the humidified flow; and
  a controller configured to determine an absolute humidity of the ambient air from the signals generated by the relative humidity sensor and the first temperature sensor and to control the first heating element to provide a predetermined relative humidity to the flow of breathable gas based on a comparison between a the determined absolute humidity of the ambient air and a condition of the breathable gas within the respiratory apparatus,
  wherein the controller is configured to control the second heating element in response to the signals from the second temperature sensor to provide the humidified flow at the second end of the delivery hose at a predetermined temperature and the predetermined relative humidity,
  wherein the controller is configured to determine a change in the rate of the flow of breathable gas and control the second heating element to adjust the predetermined temperature when the change in the flow rate exceeds a predetermined flow rate change, and wherein the controller is configured to control the second heating element to increase the predetermined temperature when the change in the flow rate exceeds a predetermined decrease in the flow rate.

63. A humidifier according to claim 62, wherein the controller is configured to control the second heating element to increase the predetermined temperature above a saturation temperature.

64. A humidifier according to claim 63, wherein the controller is configured to control the first heating element to decrease the temperature of the supply of water when the change in the flow rate exceeds the predetermined decrease in the flow rate.

65. A humidifier according to claim 64, wherein the controller is configured to control the second heating element to decrease the predetermined temperature at a predetermined time after the first heating element is controlled to decrease the temperature of the supply of water.

* * * * *

UNITED STATES PATENT AND TRADEMARK OFFICE
CERTIFICATE OF CORRECTION

PATENT NO. : 9,802,022 B2  Page 1 of 1
APPLICATION NO. : 12/397850
DATED : October 31, 2017
INVENTOR(S) : Smith et al.

It is certified that error appears in the above-identified patent and that said Letters Patent is hereby corrected as shown below:

In the Claims

In Claim 45, at Column 38, Line 36, "wherein AHp is predetermined humidity," should read "wherein AHp is the predetermined humidity"

Signed and Sealed this
Twenty-eighth Day of August, 2018

Andrei Iancu
*Director of the United States Patent and Trademark Office*